(12) United States Patent
Hunt

(10) Patent No.: US 10,973,693 B2
(45) Date of Patent: Apr. 13, 2021

(54) NEGATIVE PRESSURE WOUND THERAPY APPARATUS AND METHODS

(71) Applicant: Smith & Nephew PLC, Watford (GB)

(72) Inventor: Allan Kenneth Frazer Grugeon Hunt, Beverley (GB)

(73) Assignee: Smith & Nephew PLC, Watford (GB)

( * ) Notice: Subject to any disclaimer, the term of this patent is extended or adjusted under 35 U.S.C. 154(b) by 579 days.

(21) Appl. No.: 15/574,790

(22) PCT Filed: May 18, 2016

(86) PCT No.: PCT/EP2016/061139
§ 371 (c)(1),
(2) Date: Nov. 16, 2017

(87) PCT Pub. No.: WO2016/184913
PCT Pub. Date: Nov. 24, 2016

(65) Prior Publication Data
US 2018/0140466 A1    May 24, 2018

Related U.S. Application Data

(60) Provisional application No. 62/332,411, filed on May 5, 2016, provisional application No. 62/163,170, filed on May 18, 2015.

(51) Int. Cl.
*A61F 13/02* (2006.01)
*A61M 1/00* (2006.01)
*A61F 13/00* (2006.01)

(52) U.S. Cl.
CPC .... *A61F 13/0216* (2013.01); *A61F 13/00068* (2013.01); *A61M 1/009* (2014.02);
(Continued)

(58) Field of Classification Search
CPC .............. A61F 13/0216; A61F 13/0068; A61F 13/00068; A61F 13/0066; A61F 13/0072;
(Continued)

(56) References Cited

U.S. PATENT DOCUMENTS

D239,019 S    3/1976  Flinn
4,498,850 A   2/1985  Perlov et al.
(Continued)

FOREIGN PATENT DOCUMENTS

CN          103357076      10/2013
DE       10 2015 21516      2/2017
(Continued)

OTHER PUBLICATIONS

International Search Report and Written Opinion, re PCT Application No. PCT/EP2016/061139, dated Oct. 12, 2016.
(Continued)

*Primary Examiner* — Ariana Zimbouski
(74) *Attorney, Agent, or Firm* — Knobbe, Martens, Olson & Bear, LLP

(57) ABSTRACT

A device and method for treating a wound of a patient with negative pressure is provided. The device comprises a pump chamber that has at least one moveable side of the chamber. The moveable side moves between an intake stroke and an exhaust stroke upon application of an electrical potential. Fluid is drawn into the pump chamber during the intake stroke and expelled from the pump chamber during the exhaust stroke. The pump system may have a magnetic or a piezoelectric element that drives the movement of the pump chamber side.

20 Claims, 20 Drawing Sheets

(52) U.S. Cl.
CPC ......... *A61M 1/0066* (2013.01); *A61M 1/0011* (2013.01); *A61M 2205/0272* (2013.01); *A61M 2205/106* (2013.01); *A61M 2205/3606* (2013.01); *A61M 2205/366* (2013.01); *A61M 2205/3613* (2013.01); *A61M 2205/3693* (2013.01)

(58) Field of Classification Search
CPC .... A61M 1/00; A61M 1/009; A61M 5/14586; A61M 5/14228; A61M 2025/1012; A61M 1/066; A61M 1/0072; A61M 1/0088; F04B 43/026; F04B 43/04; B81B 3/00; F40B 43/08
USPC .................................... 417/477.2; 604/65–67
See application file for complete search history.

(56) References Cited

U.S. PATENT DOCUMENTS

| | | | |
|---|---|---|---|
| 4,731,076 A * | 3/1988 | Noon | A61M 1/1058 128/DIG. 3 |
| D357,735 S | 4/1995 | McPhee | |
| 5,514,088 A | 5/1996 | Zakko | |
| 5,712,795 A | 1/1998 | Layman et al. | |
| 6,027,490 A | 2/2000 | Radford et al. | |
| 6,203,291 B1 * | 3/2001 | Stemme | F04B 43/043 137/833 |
| 6,232,680 B1 * | 5/2001 | Bae | H01L 23/467 257/E23.099 |
| 6,396,407 B1 | 5/2002 | Kobayashi | |
| D475,132 S | 5/2003 | Randolph | |
| 7,004,915 B2 | 2/2006 | Boynton et al. | |
| 7,022,113 B2 | 4/2006 | Lockwood et al. | |
| 7,070,584 B2 | 7/2006 | Johnson et al. | |
| 7,214,202 B1 | 5/2007 | Vogel et al. | |
| D581,042 S | 11/2008 | Randolph et al. | |
| D590,934 S | 4/2009 | Randolph et al. | |
| D602,582 S | 10/2009 | Pidgeon et al. | |
| D602,583 S | 10/2009 | Pidgeon et al. | |
| D602,584 S | 10/2009 | Pidgeon et al. | |
| 7,608,066 B2 | 10/2009 | Vogel | |
| 7,611,500 B1 | 11/2009 | Lina et al. | |
| D625,801 S | 10/2010 | Pidgeon et al. | |
| 7,857,806 B2 | 12/2010 | Karpowicz et al. | |
| D630,313 S | 1/2011 | Pidgeon et al. | |
| D630,725 S | 1/2011 | Pidgeon et al. | |
| 7,927,319 B2 | 4/2011 | Lawhorn | |
| D645,137 S | 9/2011 | Mario Gonzalez | |
| 8,021,348 B2 | 9/2011 | Risk, Jr. et al. | |
| 8,062,272 B2 | 11/2011 | Weston | |
| 8,066,243 B2 | 11/2011 | Svedman et al. | |
| 8,070,735 B2 | 12/2011 | Koch et al. | |
| D654,164 S | 2/2012 | Cole et al. | |
| D660,409 S | 5/2012 | Taggerty et al. | |
| 8,215,929 B2 * | 7/2012 | Shen | A61M 1/0066 417/360 |
| 8,216,197 B2 | 7/2012 | Simmons et al. | |
| 8,226,620 B2 | 7/2012 | Giezendanner et al. | |
| 8,308,714 B2 | 11/2012 | Weston et al. | |
| 8,317,774 B2 | 11/2012 | Adahan | |
| 8,366,692 B2 | 2/2013 | Weston | |
| 8,409,160 B2 * | 4/2013 | Locke | A61M 1/0066 604/319 |
| 8,480,641 B2 | 7/2013 | Jacobs | |
| 8,641,693 B2 | 2/2014 | Locke et al. | |
| 8,668,677 B2 | 3/2014 | Eckstein et al. | |
| 8,827,967 B2 | 9/2014 | Lawhorn | |
| 8,858,517 B2 | 10/2014 | Pan et al. | |
| 8,905,985 B2 | 12/2014 | Allen et al. | |
| 9,084,845 B2 | 7/2015 | Adie et al. | |
| 9,138,531 B2 | 9/2015 | Yodfat et al. | |
| 9,199,010 B2 | 12/2015 | Yao et al. | |
| D750,222 S | 2/2016 | Chang | |
| D750,235 S | 2/2016 | Maurice | |
| D750,236 S | 2/2016 | Maurice | |
| D757,260 S | 5/2016 | Lombardi, III et al. | |
| 9,327,063 B2 | 5/2016 | Locke et al. | |
| 9,333,281 B2 | 5/2016 | Giezendanner et al. | |
| D764,047 S | 8/2016 | Bjelovuk et al. | |
| D764,048 S | 8/2016 | Bjelovuk et al. | |
| D764,653 S | 8/2016 | Bjelovuk et al. | |
| D764,654 S | 8/2016 | Bjelovuk et al. | |
| 9,415,199 B2 | 8/2016 | Tsai | |
| 9,427,505 B2 | 8/2016 | Askem et al. | |
| D765,830 S | 9/2016 | Bjelovuk et al. | |
| 9,445,948 B2 | 9/2016 | Smola | |
| D773,658 S | 12/2016 | Bow | |
| 9,586,036 B2 | 3/2017 | Masuda et al. | |
| D788,293 S | 5/2017 | Eckstein | |
| D791,939 S | 7/2017 | Tuturro et al. | |
| D792,586 S | 7/2017 | Becker | |
| 9,737,649 B2 | 8/2017 | Begin et al. | |
| D797,275 S | 9/2017 | Evans et al. | |
| D802,744 S | 11/2017 | Bjelovuk et al. | |
| 9,901,664 B2 | 2/2018 | Askem | |
| D813,374 S | 3/2018 | Bjelovuk et al. | |
| D814,016 S | 3/2018 | Bjelovuk et al. | |
| D815,726 S | 4/2018 | Bjelovuk et al. | |
| D815,727 S | 4/2018 | Bjelovuk et al. | |
| D820,980 S | 6/2018 | Maurice | |
| 9,923,401 B2 | 10/2018 | Jung | |
| 10,143,785 B2 | 12/2018 | Adams et al. | |
| 10,155,070 B2 | 12/2018 | Childress et al. | |
| D852,356 S | 6/2019 | Steele et al. | |
| 2002/0013545 A1 | 1/2002 | Soltanpour et al. | |
| 2002/0030002 A1 | 3/2002 | Verkaart et al. | |
| 2002/0098097 A1 * | 7/2002 | Singh | B01L 3/5027 417/413.1 |
| 2004/0068224 A1 | 4/2004 | Couvillon et al. | |
| 2006/0281398 A1 * | 12/2006 | Yokomizo | G06F 1/203 454/184 |
| 2009/0216205 A1 * | 8/2009 | Ryan | A61L 11/00 604/319 |
| 2009/0299306 A1 | 12/2009 | Buan | |
| 2010/0244780 A1 | 9/2010 | Turner | |
| 2011/0006876 A1 | 1/2011 | Moberg et al. | |
| 2011/0060300 A1 | 3/2011 | Weig et al. | |
| 2011/0076170 A1 * | 3/2011 | Fujisaki | F04B 45/047 417/415 |
| 2011/0196291 A1 | 8/2011 | Vischer et al. | |
| 2012/0289913 A1 | 11/2012 | Eckstein et al. | |
| 2013/0012772 A1 | 1/2013 | Gunday et al. | |
| 2013/0025692 A1 | 1/2013 | Heide et al. | |
| 2013/0237937 A1 | 9/2013 | Ramella et al. | |
| 2013/0267917 A1 | 10/2013 | Pan et al. | |
| 2013/0274718 A1 | 10/2013 | Yao et al. | |
| 2014/0023533 A1 * | 1/2014 | Ishii | F04B 45/047 417/413.1 |
| 2014/0276488 A1 | 9/2014 | Locke et al. | |
| 2015/0174320 A1 | 6/2015 | Grant et al. | |
| 2015/0231021 A1 | 8/2015 | Smith et al. | |
| 2015/0246164 A1 | 9/2015 | Heaton et al. | |
| 2015/0320916 A1 | 11/2015 | Croteau et al. | |
| 2016/0015872 A1 | 1/2016 | Luckemeyer et al. | |
| 2016/0213843 A1 | 7/2016 | Despa et al. | |
| 2016/0250398 A1 | 9/2016 | Barr et al. | |
| 2016/0271305 A1 | 9/2016 | Kurihara et al. | |
| 2016/0303358 A1 | 10/2016 | Croizat et al. | |
| 2017/0165405 A1 | 6/2017 | Muser et al. | |
| 2017/0189666 A1 | 7/2017 | Sealfon et al. | |
| 2017/0216501 A1 | 8/2017 | Armstrong et al. | |
| 2017/0296716 A1 | 10/2017 | Middleton et al. | |
| 2017/0319758 A1 | 11/2017 | Eddy et al. | |
| 2017/0354767 A1 | 12/2017 | Carr et al. | |
| 2017/0354768 A1 | 12/2017 | Bushko et al. | |
| 2018/0021178 A1 | 1/2018 | Locke et al. | |
| 2018/0250459 A1 | 9/2018 | Kimball et al. | |
| 2018/0264181 A1 | 9/2018 | Gregory et al. | |
| 2018/0308578 A1 | 10/2018 | Armstrong et al. | |
| 2018/0318476 A1 | 11/2018 | Askem et al. | |
| 2019/0167867 A1 | 6/2019 | Adams et al. | |

(56) References Cited

U.S. PATENT DOCUMENTS

| | | | |
|---|---|---|---|
| 2019/0388279 A1 | 12/2019 | Hartwell et al. | |
| 2020/0121833 A9 | 4/2020 | Askem et al. | |

FOREIGN PATENT DOCUMENTS

| EP | 3 037 116 | 6/2016 |
| EP | 3 124 059 | 2/2017 |
| EP | 3 124 060 | 2/2017 |
| FR | 2939320 A1 | 6/2010 |
| GB | 1220857 A | 1/1971 |
| JP | S56-047279 | 4/1981 |
| JP | H01-101978 | 4/1989 |
| JP | H07-96029 | 4/1995 |
| JP | 2007-218241 | 8/2007 |
| JP | 2010-502405 | 1/2010 |
| WO | WO-9605873 A1 | 2/1996 |
| WO | WO 2000/061206 | 10/2000 |
| WO | WO 03/081762 A1 | 10/2003 |
| WO | WO 2008/033788 | 3/2008 |
| WO | WO 2008/039223 | 4/2008 |
| WO | WO 2008/135997 A2 | 11/2008 |
| WO | WO-2009071924 A1 | 6/2009 |
| WO | WO 2011/075706 A1 | 6/2011 |
| WO | WO-2011094410 A2 | 8/2011 |
| WO | WO 2012/004298 | 1/2012 |
| WO | WO 2012/100624 | 8/2012 |
| WO | WO 2013/015827 | 1/2013 |
| WO | WO-2013078214 A1 | 5/2013 |
| WO | WO 2013/171585 A2 | 11/2013 |
| WO | WO 2014/115819 | 7/2014 |
| WO | WO 2014/164655 | 10/2014 |
| WO | WO 2015/197462 | 12/2015 |
| WO | WO 2017/160412 | 9/2017 |

OTHER PUBLICATIONS

"Battery Charger", Wikipedia, accessed Nov. 9, 2018, in 12 pages. URL: https://web.archive.org/web/20181109005000/https://en.wikipedia.org/wiki/Battery_charger.

International Preliminary Report on Patentability for Application No. PCT/EP2016/061139, dated Nov. 30, 2017, 12 pages.

* cited by examiner

NEGATIVE PRESSURE WOUND THERAPY APPARATUS AND METHODS

CROSS-REFERENCE TO RELATED APPLICATIONS

This application is a national stage application under 35 U.S.C. § 371 of International Application No. PCT/EP2016/061139, filed on May 18, 2016, which published in English as WO 2016/184913 A1 on Nov. 24, 2016, and which claims priority benefit of U.S. Patent Application No. 62/163,170, filed on May 18, 2015, and U.S. Patent Application No. 62/332,411, filed on May 5, 2016.

BACKGROUND

Field

Embodiments or arrangements disclosed herein relate to methods and apparatuses for dressing and treating a wound with topical negative pressure (TNP) therapy. For example but without limitation, any embodiments disclosed herein relate to treating a wound with reduced pressure provided from a pump kit. Although not required, any embodiments of the pump kit can be sterile. As another non-limiting example, any embodiments disclosed herein relate to apparatuses and methods for controlling the operation of a TNP system.

Background

Many different types of wound dressings are known for aiding in the healing process of a human or animal. These different types of wound dressings include many different types of materials and layers, for example, pads such as gauze pads and/or foam pads. Topical negative pressure ("TNP") therapy, sometimes referred to as vacuum assisted closure, negative pressure wound therapy, or reduced pressure wound therapy, is widely recognized as a beneficial mechanism for improving the healing rate of a wound. Such therapy is applicable to a broad range of wounds such as incisional wounds, open wounds and abdominal wounds or the like.

TNP therapy assists in the closure and healing of wounds by reducing tissue oedema; encouraging blood flow; stimulating the formation of granulation tissue; removing excess exudates, and may reduce bacterial load and thus reduce the potential for infection of the wound. Furthermore, TNP therapy permits less outside disturbance of the wound and promotes more rapid healing.

SUMMARY

Embodiments of the present disclosure relate to apparatuses and methods for wound treatment. Some of the wound treatment apparatuses described herein comprise a pump system for providing negative pressure to a wound site. Wound treatment apparatuses may also comprise wound dressings that may be used in combination with the pump systems described herein, and connectors for connecting the wound dressings to the pump systems.

In accordance with one embodiment, a pump assembly is provided. The pump assembly comprises a first membrane and a second membrane that together define a chamber therebetween. The pump assembly further comprises a first magnetic actuator proximate an inner surface of the first membrane and a second magnetic actuator proximate an inner surface of the second membrane. One or both of the first and second magnetic actuators can provide a magnetic field that applies a magnetic force to the first and second magnetic actuators and to the first and second membranes, causing the membranes to move toward and way from each other to pump a fluid through the chamber.

Optionally, one or more of the first and second magnetic actuators is an electromagnet configured to generate a magnetic field upon the passing of a current therethrough.

Optionally, one or more of the first and second magnetic actuators is a permanent magnet that provides a permanent magnetic field.

In accordance with another embodiment an apparatus for use in negative pressure wound therapy is provided. The apparatus comprises a pump system. The pump system comprises a pump assembly that comprises a pump chamber having an interior surface, an exterior surface, a first side, a second side generally opposite the first side, an inlet and an outlet. The pump assembly further comprises a first magnetic actuator coupled to the first side of the pump chamber, and a second magnetic actuator coupled to the second side of the pump chamber. One or both of the first and second magnetic actuators is an electromagnet that is actuatable to generate a magnetic field that applies a force on one of both of the first and second magnetic actuators to move the pump chamber between an extended position and a collapsed position to pump a fluid through the chamber.

In accordance with another embodiment, a combination of a wound dressing and the apparatus described in the previous paragraph is provided, wherein the pump system is configured to pump a fluid from the wound dressing during a negative pressure wound therapy.

In accordance with another embodiment, a wound dressing for use in negative pressure wound therapy is provided. The wound dressing comprises a dressing body comprising one or more layers and configured to be removably disposed over a wound site. The wound dressing further comprises one or more pump assemblies disposed over and fluidically coupled to at least one of said one or more layers and configured to pump a fluid from said wound site. Each of the one or more pump assemblies comprises a pump chamber defined by an interior surface of a first side and a second side generally opposite the first side, an inlet and an outlet. Each pump assembly further comprises a first magnetic actuator coupled to the interior surface of the first side of the pump chamber, and a second magnetic actuator coupled to the interior surface of the second side of the pump chamber. One or both of the first and second magnetic actuators is an electromagnet that is actuatable to generate a magnetic field that applies a force on one of both of the first and second magnetic actuators to move the pump chamber between an extended position and a collapsed position to pump a fluid through the chamber.

An apparatus for use in negative pressure wound therapy, comprising a pump system comprising a pump assembly comprising a pump chamber having an interior surface, an exterior surface, a first side, a second side generally opposite the first side, an inlet and an outlet; a first magnetic actuator coupled to the first side of the pump chamber; and a second magnetic actuator coupled to the second side of the pump chamber, wherein one or both of the first and second magnetic actuators is an electromagnet that is actuatable to generate a magnetic field that applies a force on one of both of the first and second magnetic actuators to move the pump chamber between an extended position and a collapsed position to pump a fluid through the chamber, wherein both the first and second magnetic actuators comprise electromagnets, and wherein the electromagnet of the first magnetic actuator and the electromagnet of the second magnetic actuator are oppositely wound along a longitudinal axis of the electromagnets, the electromagnet of the first magnetic actuator configured to be supplied with an electric current in a first phase and the electromagnet of the second magnetic actuator configured to be supplied with an electric current in a second phase different than the first phase to operate the pump assembly.

An apparatus for use in negative pressure wound therapy, comprising a pump system comprising a pump assembly comprising a pump chamber having an interior surface, an exterior surface, a first side, a second side generally opposite the first side, an inlet and an outlet; a first magnetic actuator coupled to the first side of the pump chamber; and a second magnetic actuator coupled to the second side of the pump chamber, wherein one or both of the first and second magnetic actuators is an electromagnet that is actuatable to generate a magnetic field that applies a force on one of both of the first and second magnetic actuators to move the pump chamber between an extended position and a collapsed position to pump a fluid through the chamber, wherein the pump assembly and the second pump assembly are fluidically coupled in series, wherein the pump assembly is operated in a first phase and the second pump assembly is operated in a second phase opposite to the first phase to facilitate movement of fluid through the pump system, wherein the pump assembly and the second pump assembly are fluidically coupled in parallel, and wherein the pump assembly and second pump assembly are operated in a same phase.

BRIEF DESCRIPTION OF THE DRAWINGS

Embodiments of the present disclosure will now be described hereinafter, by way of example only, with reference to the accompanying drawings in which.

DETAILED DESCRIPTION

Figure 1:
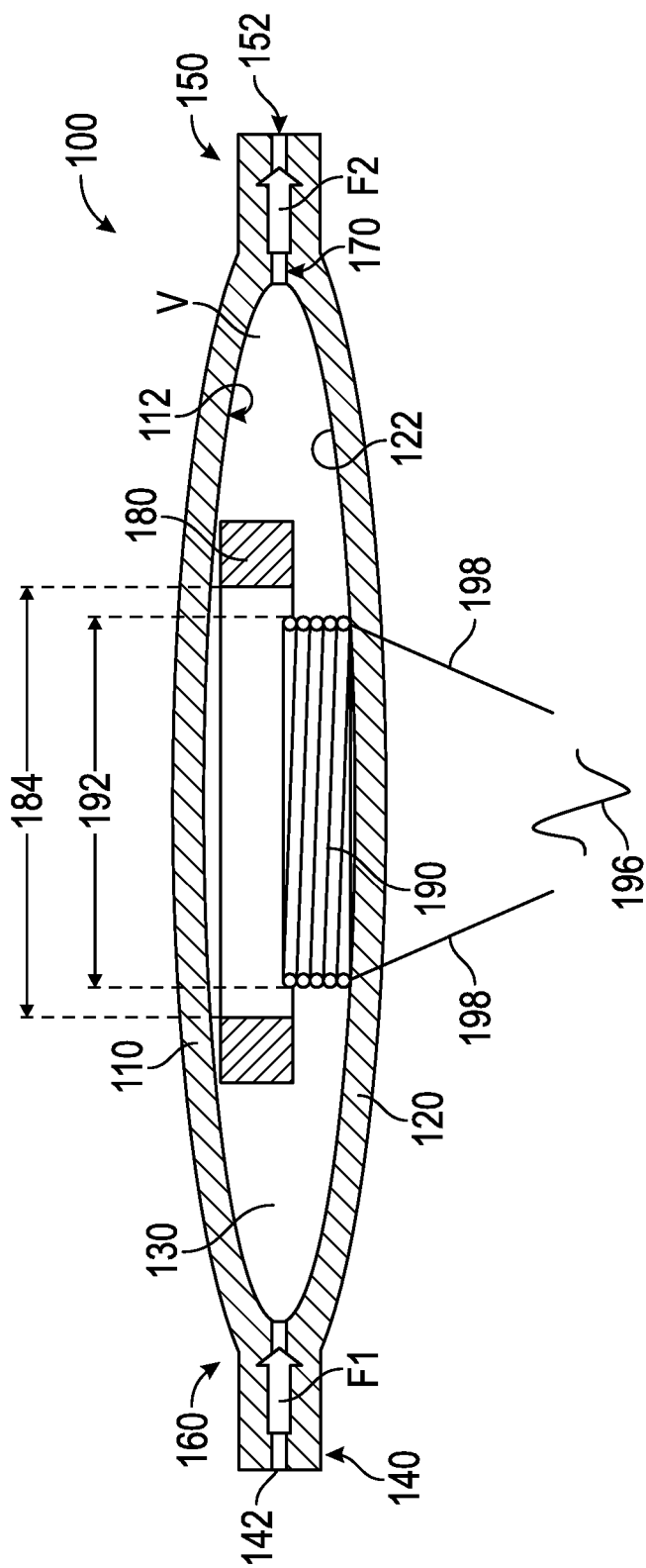
FIG. 1 is a schematic cross-sectional view of an embodiment of a pump assembly.

Embodiments disclosed herein relate to apparatuses and methods of treating a wound with reduced pressure, including pump and wound dressing components and apparatuses. The apparatuses and components comprising the wound overlay and packing materials, if any, are sometimes collectively referred to herein as dressings.

It will be appreciated that throughout this specification reference is made to a wound. It is to be understood that the term wound is to be broadly construed and encompasses open and closed wounds in which skin is torn, cut or punctured or where trauma causes a contusion, or any other surficial or other conditions or imperfections on the skin of a patient or otherwise that benefit from reduced pressure treatment. A wound is thus broadly defined as any damaged region of tissue where fluid may or may not be produced. Examples of such wounds include, but are not limited to, acute wounds, chronic wounds, surgical incisions and other incisions, subacute and dehisced wounds, traumatic wounds, flaps and skin grafts, lacerations, abrasions, contusions, burns, diabetic ulcers, pressure ulcers, stoma, surgical wounds, trauma and venous ulcers or the like. In some embodiments disclosed herein, the components of the TNP system described herein can be particularly suited for incisional wounds that exude a small amount of wound exudate.

It will be understood that embodiments of the present disclosure are generally applicable to use in topical negative pressure ("TNP") therapy systems. Briefly, negative pressure wound therapy assists in the closure and healing of many forms of "hard to heal" wounds by reducing tissue oedema, encouraging blood flow and granular tissue formation, and/or removing excess exudate and can reduce bacterial load (and thus infection risk). In addition, the therapy allows for less disturbance of a wound leading to more rapid healing. TNP therapy systems can also assist in the healing of surgically closed wounds by removing fluid and by helping to stabilize the tissue in the apposed position of closure. A further beneficial use of TNP therapy can be found in grafts and flaps where removal of excess fluid is important and close proximity of the graft to tissue is required in order to ensure tissue viability.

As is used herein, reduced or negative pressure levels, such as −X mmHg, represent pressure levels that are below standard atmospheric pressure, which corresponds to 760 mmHg (or 1 atm, 29.93 inHg, 101.325 kPa, 14.696 psi, etc.). Accordingly, a negative pressure value of −X mmHg reflects absolute pressure that is X mmHg below 760 mmHg or, in other words, an absolute pressure of (760−X) mmHg. In addition, negative pressure that is "less" or "smaller" than X mmHg corresponds to pressure that is closer to atmospheric pressure (e.g., −40 mmHg is less than −60 mmHg). Negative pressure that is "more" or "greater" than −X mmHg corresponds to pressure that is further from atmospheric pressure (e.g., −80 mmHg is more than −60 mmHg).

The operating negative pressure range for some embodiments of the present disclosure can be between approximately −10 mmHg to −200 mmHg, between −20 mmHg to −150 mmHg, between approximately −45 mm Hg and approximately −100 mm Hg nominal operating pressure (e.g., between −45 mm Hg and −100 mm Hg, inclusive) with approximately +/−12% hysteresis during operation, any subrange within this range, or any other range as desired. In one embodiment, the nominal operating negative pressure can be −80 mm Hg, and operate between −70 mm Hg and −90 mm Hg.

In some embodiments, the pump system can be included as part of a wound treatment apparatus which can include, for example, a wound dressing. In some embodiments, the pump system can be separate from the wound dressing as a standalone unit. This can beneficially allow the pump system to be positioned at a different location away from the wound dressing. In some embodiments, the pump system can be attached to (e.g., incorporated in) the wound dressing to form a single unit. This can potentially reduce the form factor of the wound treatment apparatus and reduce the length of a conduit attaching the pump system to the wound dressing.

In some embodiments, the pump system can be configured to operate in a canisterless system, in which the wound dressing retains exudate aspirated from the wound. Such a dressing can include a filter, such as a hydrophobic filter, that prevents passage of liquids downstream of the dressing (toward the pump system). In other embodiments, the pump system can be configured to operate in a system having a canister for storing at least part of exudate aspirated from the wound. Such canister can include a filter, such as a hydrophobic filter, that prevents passage of liquids downstream of the dressing (toward the pump system). In yet other embodiments, both the dressing and the canister can include filters that prevent passage of liquids downstream of the dressing and the canister.

The pump system embodiments described herein can have a compact, small size. In some embodiments, the pump can have a diameter of between about 5 mm to 400 mm, between 10 mm to 200 mm, between 20 mm to 100 mm, between about 8 mm and about 20 mm, any subrange within these ranges, or any other range desired. The pump system can have a thickness of between approximately 1 mm to 30 mm, between 2 mm to 20 mm, between 3 mm to 10 mm, any subrange within these ranges or other range desired. In one embodiment, the thickness can be less than about 4 mm. In some embodiments, grids of the pumps can encompass areas of up to about 100 mm×100 mm.

FIG. 1 shows a cross-sectional view of one embodiment of a pump assembly 100. The pump assembly 100 has a first membrane 110 and a second membrane 120 that define a chamber 130 therebetween. The first and second membranes 110, 120 can be made of a flexible material, such as closed cell foam or open cell foam with an impermeable skin. However, the first and second membranes 110, 120 can be made of other suitable materials, such as Polyurethane, Polyethylene terephthalate (PET), and silicone. The first and second membranes 110, 120 can optionally be sealed together along their respective edges to define the chamber 130. For example, edges of the first and second membranes 110, 120 can be sealed via welding (e.g., ultrasonic, heat, etc.) or via an adhesive. The chamber 130 can have a volume V of between about 20 mm$^3$ and about 1000 mm$^3$.

The pump assembly 100 has an inlet portion 140 with an inlet passage 142 in fluid communication with the chamber 130. The pump assembly 100 has an outlet portion 150 with an outlet passage 152 in fluid communication with the chamber 130. The inlet portion 140 optionally includes a one-way valve 160 that allows fluid flow through the inlet passage 142 into the chamber 130 but inhibits (e.g., prevents) flow from the chamber 130 into the inlet passage 142 (e.g., inhibits reverse flow into the inlet passage 142). The outlet portion 150 optionally includes a one-way valve 170 that allows fluid flow from the chamber 130 and through the outlet passage 152 but inhibits (e.g., prevents) flow from the outlet passage 152 into the chamber 130 (e.g., inhibits reverse flow into the chamber 130).

With continued reference to FIG. 1, the pump assembly 100 includes first magnetic actuator, such as a magnet 180, proximate an inner surface 112 of the first membrane 110 and includes a second magnetic actuator, such as an electromagnet 190, proximate an inner surface 122 of the second membrane 120. The electromagnet 190 can optionally be a voice coil. In one embodiment, the magnet 180 is attached to the inner surface 112 and the electromagnet 190 is attached to the inner surface 122. In the illustrated embodiment, the electromagnet 190 is cylindrical and has a diameter 192 and the magnet 180 is annular and has an opening 182 with an inner diameter 184 that is greater than the diameter 192 of the electromagnet 190, allowing the electromagnet 190 to at least partially extend into the opening 182 when the membranes 110, 120 move toward each other, as further discussed below.

In some embodiments, the electromagnet 190 can be in the form of a coil having a body formed from a length of wound conductive wire, such as without limitation copper wire or any other electrically conductive material. Upon application of a current through the body of the electromagnet 190, a magnetic field can be generated generally directed along a direction parallel to an axial centerline for the coil. As should be understood, the direction of the magnetic field can be reversed by reversing the direction of current flow through the coil. To provide current to the coil, an electrical conduit 198 can be connected to both ends of the coil. In some embodiments, the electrical conduit 198 can be a flexible printed circuit (FPC) attached to a circuit board (not shown). Other types of electrical conduits, such as elongate wires, can be used.

In some embodiments, the coil can be formed by winding approximately 160 turns of wire, or from approximately 100 turns or less to 200 turns or more of wire, which can be but is not required to be, 42 gauge (approximately 0.102 mm diameter) wire. The wire used can be self-bonding wire that bonds to adjacent sections of wire upon application of heat. The wire can also be non-self-bonding wire. In some embodiments, approximately 200 turns of wire, or up to approximately 260 turns of wire, can be used to form the coil. Increasing the number of turns of wire can potentially reduce ohmic losses and improve the overall efficiency of the pump assembly 100 by between approximately 22% and approximately 24%. As the number of turns of wire is increased, thereby increasing the efficiency of the pump, the size or thickness of the magnet can be decreased, thereby reducing the magnetic field outside of the pump assembly 100 that can potentially interfere with the function of pacemakers and other implanted cardiac devices (ICDs).

In operation, the electromagnet 190 is selectively supplied with an electric current (e.g., alternating current) from a power source 196. The electric current can flow through the electromagnet 190 to generate a magnetic field such that a magnetic force can be applied to the electromagnet 190 by virtue of the permanent magnetic field provided by the magnet 180. The magnetic force applied to the electromagnet 190 by the magnet 180 is transmitted to the first and second membranes 110, 120, which cause the membranes 110, 120 to move toward and away from each other. For example, the membranes 110, 120 can move toward each other when current flows through the electromagnet 190 in one direction, and the membranes 110, 120 can move away from each other when current flows though the electromagnet 190 in a second direction opposite to the first direction to reverse the direction of the magnetic field generated in the electromagnet 190.

The pump assembly 100 can pump a fluid (e.g., air) through the chamber 130 via reciprocation of the membranes 110, 120 toward and away from each other due to forces generated by the electromagnet 190 relative to the magnet 180. When the membranes 110, 120 move away from each other, fluid is drawn into the chamber 130 through the inlet passage 142 along a direction F1. Notably, as the membranes 110, 120 move apart, flow of fluid from the outlet passage 152 into the chamber 130 is inhibited by the one-way valve 170 in the outlet portion 150. When the membranes 110, 120 move toward each other, fluid exits the chamber 130 through the outlet passage 152 along direction F2. Notably, as the membranes 110, 120 move toward each other, flow of fluid from the chamber 130 is inhibited from passing into the inlet passage 142 by the one-way valve 160. Therefore, the one-way valves 160, 170 ensure that fluid flows through the chamber 130 in one direction (e.g., along direction F1 and F2) to thereby pump the fluid from an upstream location (e.g., a wound location).

In one embodiment, the one-way valves 160, 170 are separate components disposed in the inlet and outlet passages 142, 152, respectively. In another embodiment, the one-way valves 160, 170 are integrally formed with the membranes 110, 120. For example, each of the one-way valves 160, 170 can be formed by a directional piercing through walls of the membranes 110, 120 (e.g., where the membranes 110, 120 join the inlet and outlet portions 140, 150). Such a directional piercing can optionally define a flap that can move in one direction to allow flow through a flow passage (e.g., the inlet or outlet passage 142, 152), and that can move in an opposite direction to substantially seal the flow passage, depending on the direction of fluid flow.

In another embodiment, one or both of the one-way valves 160, 170 can include materials that change shape when exposed to an electrical potential (e.g., a temporary potential, a continuous potential), such as liquid crystals, allowing the complete opening or closure of the valve 160, 170 in addition to one-way flow operation.

In another embodiment, one or both of the one-way valves 160, 170 can incorporate materials that swell on contact with a liquid. Such materials can advantageously allow the sealing of the flow passage and stopping pumping action by the pump assembly 100, for example, if a wound dressing in fluid communication with the pump assembly 100 becomes full.

Figure 2:
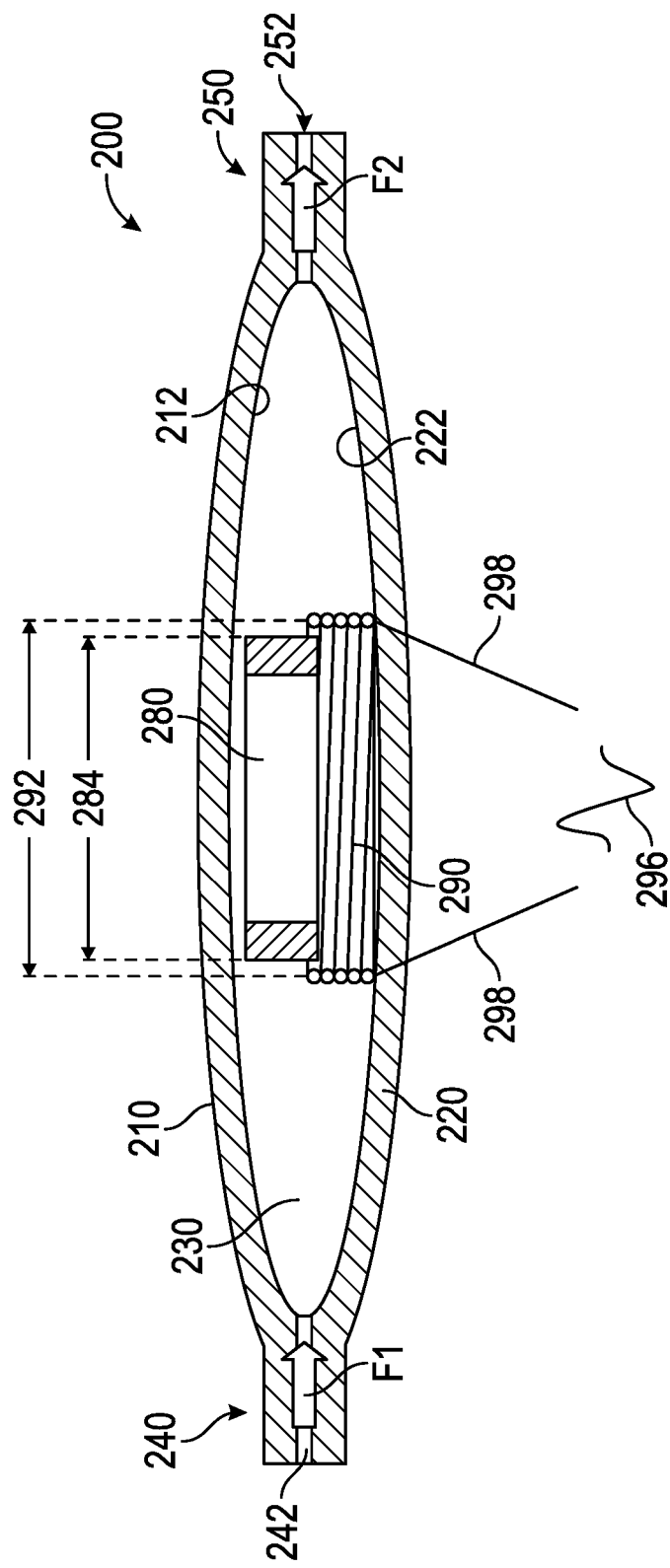
FIG. 2 is a schematic cross-sectional view of an embodiment of a pump assembly.

FIG. 2 shows another embodiment of a pump assembly 200. The pump assembly 200 is similar to the pump assembly 100 shown in FIG. 1, except as noted below. Thus, the reference numerals used to designate the various components of the pump assembly 200 are identical to those used for identifying the corresponding components of the pump assembly 100 in FIG. 1, except that the reference numerals of the pump assembly 200 begin with a "2". Therefore the description for the various components of the pump assembly 100 shown in FIG. 1 is understood to apply to the corresponding components of the pump assembly 200 in FIG. 2, except as described below.

The pump assembly 200 has a magnet 280 proximate an inner surface 212 of a first membrane 210 and an electromagnet 290, such as a voice coil, proximate an inner surface 222 of a second membrane 220. The magnet 280 is optionally cylindrical with an outer diameter 284. The electromagnet 290 is optionally cylindrical and has an inner diameter 292. The inner diameter 292 of the electromagnet 290 is larger than the outer diameter 284 of the magnet 280, allowing the magnet 280 to at least partially extend into a space defined by the inner diameter 292 of the electromagnet 290.

Figure 3:
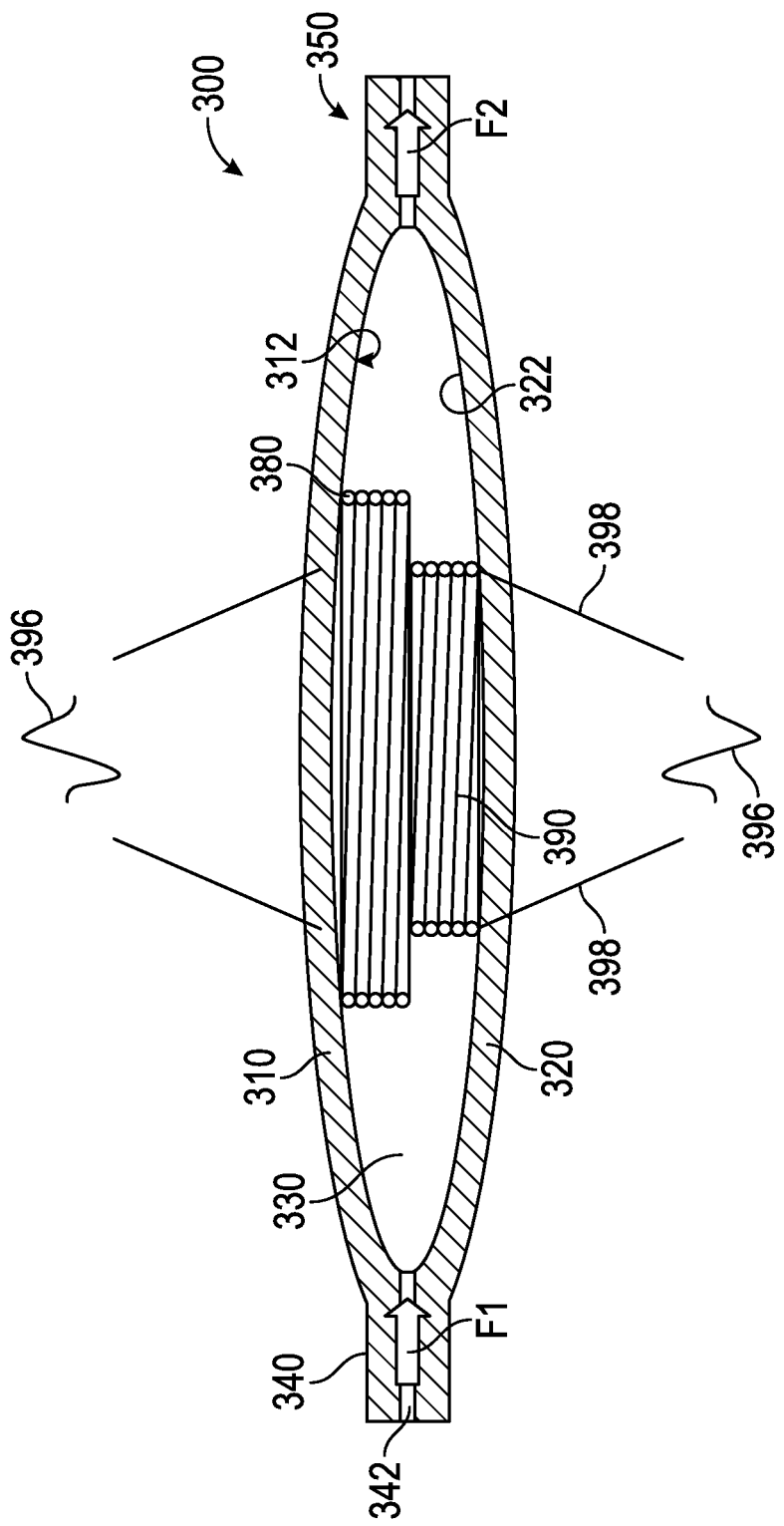
FIG. 3 is a schematic cross-sectional view of an embodiment of a pump assembly.

FIG. 3 shows another embodiment of a pump assembly 300. The pump assembly 300 is similar to the pump assembly 100 shown in FIG. 1, except as noted below. Thus, the reference numerals used to designate the various components of the pump assembly 300 are identical to those used for identifying the corresponding components of the pump assembly 100 in FIG. 1, except that the reference numerals of the pump assembly 300 begin with a "3". Therefore the description for the various components of the pump assembly 100 shown in FIG. 1 is understood to apply to the corresponding components of the pump assembly 300 in FIG. 3, except as described below.

The pump assembly 300 has a first electromagnet 380 proximate an inner surface 312 of a first membrane 310 and a second electromagnet 390 proximate an inner surface 322 of a second membrane 320. The first electromagnet 380 is optionally cylindrical with an inner diameter 384. The second electromagnet 390 is optionally cylindrical and has an outer diameter 392. The outer diameter 392 of the second electromagnet 390 is smaller than the inner diameter 384 of the first electromagnet 380, allowing the second electromagnet 390 to at least partially extend into a space defined by the inner diameter 384 of the first electromagnet 380.

In operation, the first and second electromagnets 380, 390 are selectively supplied with an electric current (e.g., alternating current) from a power source 396. For example the first electromagnet 380 can be supplied with an electric current in anti-phase to that supplied to the second electromagnet 390. The electric current can flow through the electromagnets 380, 390 to generate a magnetic field such that a magnetic force can be applied to the electromagnets 380, 390. The magnetic force applied to the electromagnets 380, 390 by the generated magnetic fields is transmitted to the first and second membranes 310, 320, which cause the membranes 310, 320 to move toward and away from each other. For example, the membranes 310, 320 can move toward each other when current flows through the electromagnets 380, 390 in one direction, and the membranes 310, 320 can move away from each other when current flows though the electromagnets 380, 390 in a second direction opposite to the first direction to reverse the direction of the magnetic field generated in the electromagnets 380, 390.

Figure 4:
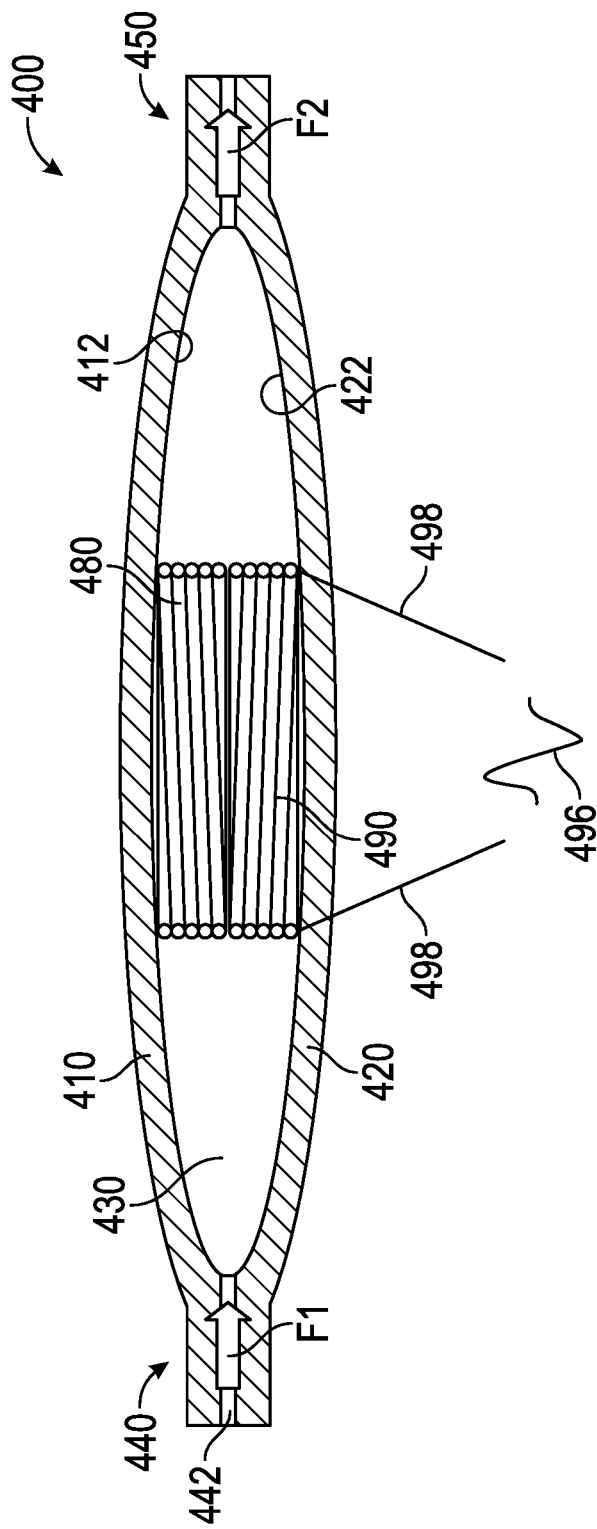
FIG. 4 is a schematic cross-sectional view of an embodiment of a pump assembly.

FIG. 4 shows another embodiment of a pump assembly 400. The pump assembly 400 is similar to the pump assembly 300 shown in FIG. 3, except as noted below. Thus, the reference numerals used to designate the various components of the pump assembly 400 are identical to those used for identifying the corresponding components of the pump assembly 300 in FIG. 3, except that the reference numerals of the pump assembly 400 begin with a "4". Therefore the description for the various components of the pump assembly 300 shown in FIG. 3 is understood to apply to the corresponding components of the pump assembly 400 in FIG. 4, except as described below.

The pump assembly 400 has a first electromagnet 480 proximate an inner surface 412 of a first membrane 410 and a second electromagnet 490 proximate an inner surface 422 of a second membrane 420. In the illustrated embodiment, the first electromagnet 480 is connected in series with the second electromagnet 490. The first electromagnet 480 is wound in the opposite direction as the second electromagnet 490.

In operation, the first and second electromagnets 480, 490 are selectively supplied with an electric current (e.g., alternating current) from a power source 496. The electric current can flow through the electromagnets 480, 490 to generate a magnetic field such that a magnetic force can be applied to the electromagnets 480, 490. The magnetic force applied to the electromagnets 480, 490 by the generated magnetic fields is transmitted to the first and second membranes 410, 420, which cause the membranes 410, 420 to move toward and away from each other. For example, the membranes 410, 420 can move toward each other when current flows through the electromagnets 480, 490 in one direction, and the membranes 410, 420 can move away from each other when current flows though the electromagnets 480, 490 in a second direction opposite to the first direction to reverse the direction of the magnetic field generated in the electromagnets 480,490.

In another embodiment (not shown), the first and second electromagnets 480, 490 can instead be connected in parallel, where the first electromagnet 480 is wound in the opposite direction than the second electromagnet 490.

Figure 5:
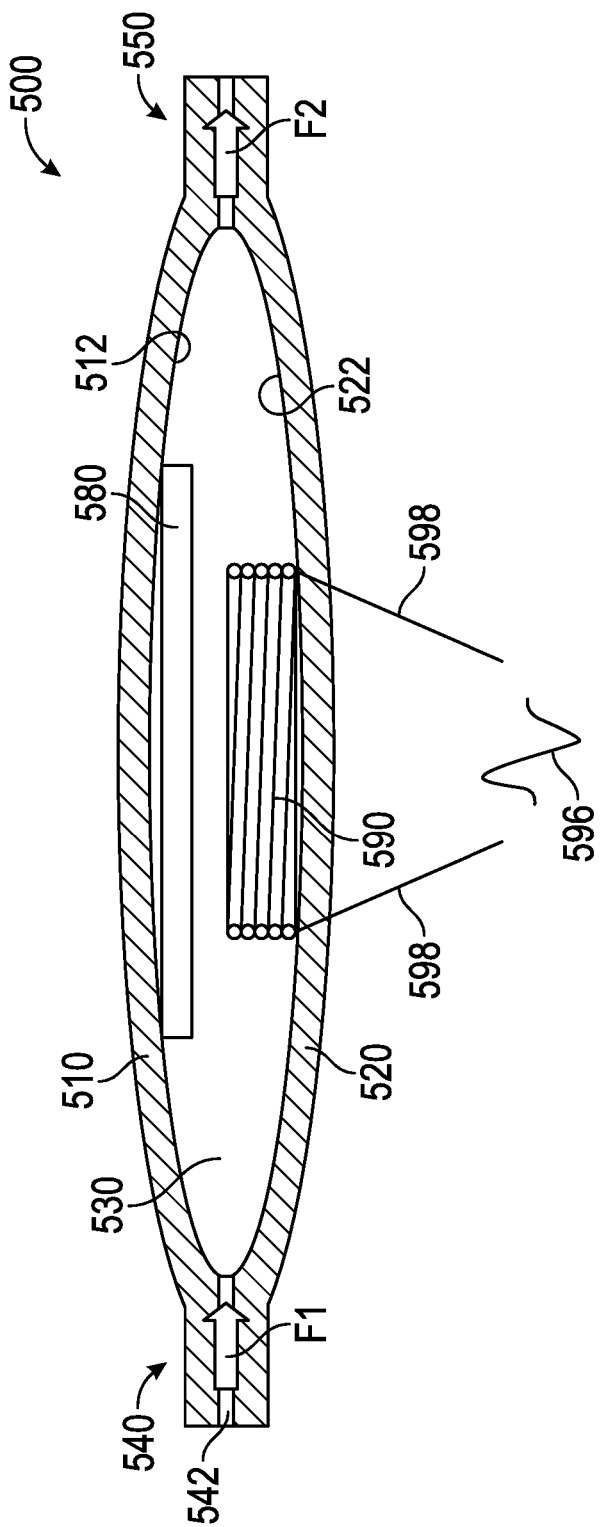
FIG. 5 is a schematic cross-sectional view of an embodiment of a pump assembly.

FIG. 5 shows another embodiment of a pump assembly 500. The pump assembly 500 is similar to the pump assembly 100 shown in FIG. 1, except as noted below. Thus, the reference numerals used to designate the various components of the pump assembly 500 are identical to those used for identifying the corresponding components of the pump assembly 100 in FIG. 1, except that the reference numerals of the pump assembly 500 begin with a "5". Therefore the description for the various components of the pump assembly 100 shown in FIG. 1 is understood to apply to the corresponding components of the pump assembly 500 in FIG. 5, except as described below.

The pump assembly 500 has a magnet 580 proximate an inner surface 512 of a first membrane 510 and an electromagnet 590 proximate an inner surface 522 of a second membrane 520. In the illustrated embodiment, the magnet 580 is shaped like a plate with a substantially planar (e.g., a planar or flat) surface 582 that faces the electromagnet 590.

Figure 6:
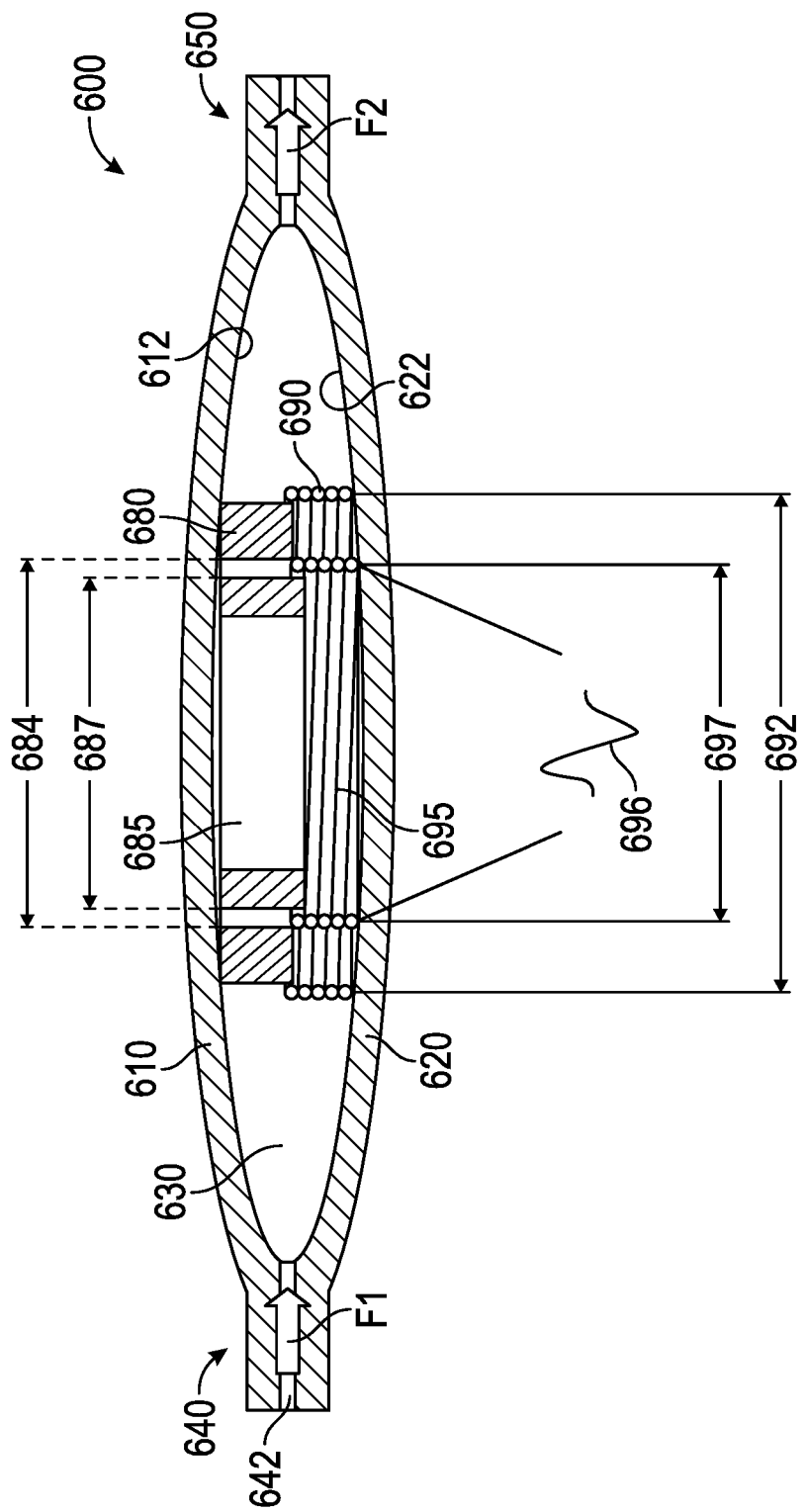
FIG. 6 is a schematic cross-sectional view of an embodiment of a pump assembly.

FIG. 6 shows another embodiment of a pump assembly 600. The pump assembly 500 is similar to the pump assembly 100 shown in FIG. 1, except as noted below. Thus, the reference numerals used to designate the various components of the pump assembly 600 are identical to those used for identifying the corresponding components of the pump assembly 100 in FIG. 1, except that the reference numerals of the pump assembly 600 begin with a "6". Therefore the description for the various components of the pump assembly 100 shown in FIG. 1 is understood to apply to the corresponding components of the pump assembly 600 in FIG. 6, except as described below.

The pump assembly 600 has a first magnet 680 proximate an inner surface 612 of a first membrane 610 and a first electromagnet 690 proximate an inner surface 622 of a second membrane 620. The pump assembly 600 also has a second magnet 685 proximate an inner surface 612 of the first membrane 610 and a second electromagnet 695 proximate an inner surface 622 of the second membrane 620. The first and second magnets 680, 685 are cylindrical with the inner diameter 684 of the first magnet 680 being greater than the outer diameter 687 of the second magnet 685, such that the first magnet 680 is disposed about the second magnet 685. The first and second electromagnets 690, 695 are cylindrical with the inner diameter 692 of the first electromagnet 690 being greater than the outer diameter 697 of the second electromagnet 695, such that the first electromagnet 690 is disposed about the second electromagnet 695. In the illustrated embodiment, the inner diameter 692 of the first electromagnet 690 is greater than an outer diameter of the first magnet 680, and an inner diameter of the second electromagnet 695 is greater than the outer diameter 687 of the second magnet 685, such that the first and second magnets 680, 685 extend at least partially within spaces in the first and second electromagnets 690, 695 during operation of the pump assembly 600. In an alternate embodiment, the first magnet 680 can have an inner diameter larger than an outer diameter of the first electromagnet 690 and the second magnet 685 can have an inner diameter larger than an outer diameter of the second electromagnet 695.

In operation, one or both of the first and second electromagnets 690, 695 are selectively supplied with an electric current (e.g., alternating current) from a power source 696. The electric current can flow through the electromagnets 690, 695 to generate a magnetic field such that a magnetic force can be applied to the electromagnets 690, 695 by virtue of the permanent magnetic field provided by the first and second magnets 680, 685. The magnetic force is transmitted to the first and second membranes 610, 620, which cause the membranes 610, 620 to move toward and away from each other. For example, the membranes 610, 620 can move toward each other when current flows through the electromagnets 690, 695 in one direction, and the membranes 610, 620 can move away from each other when current flows though the electromagnets 690, 695 in a second direction opposite to the first direction to reverse the direction of the magnetic field generated in the electromagnets 690, 695.

In some embodiments, one or more of the magnets disclosed herein (such as magnets 180, 280, 580, 680, 685) can be printed, electro-statically deposited or otherwise applied onto the surface of the membrane (e.g., membranes 110, 210). In another embodiment, one or more of the magnets disclosed herein (such as magnets 180, 280, 580, 680, 685) can be attached onto a corresponding surface of the membrane (e.g., as an adhesive patch).

In some embodiments, one or more of the electromagnets disclosed herein (such as electromagnets 190, 290, 380, 390, 480, 490, 690, 695) can be printed, electro-statically deposited or otherwise applied onto the surface of the membrane (e.g., membranes 110, 120, 210, 220, 310, 320, 410, 420). In another embodiment, one or more of the electromagnets disclosed herein (such as electromagnets 190, 290, 380, 390, 480, 490, 690, 695) can be attached onto a corresponding surface of the membrane (e.g., as an adhesive patch).

In some embodiments, one or both of the membranes (such as the membranes 110, 120, 210, 220, etc.) in each pump assembly can include a bi-stable element therein to aid the membrane in reaching a retracted or extended position by allowing the membrane to snap into the retracted and/or extended position.

In other embodiments, the pump assembly (such as the pump assemblies discussed above) can have a chamber (such as chamber 130) that is mono-stable, so that the chamber is biased toward one direction (e.g., toward moving the membranes to the expended position), and where an electropotential is applied to the electromagnet in only one direction (e.g., to move the membranes to the retracted position).

Figure 7A:
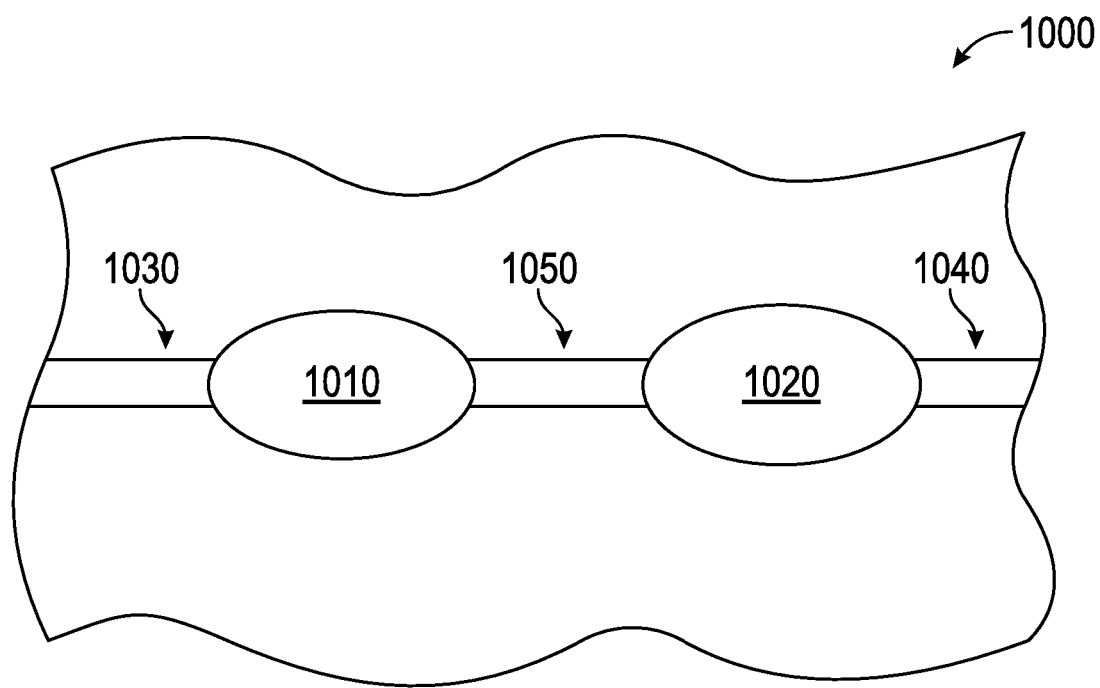
FIGS. 7A-7B show a schematic top view of an array of pump assemblies.
Figure 7B:
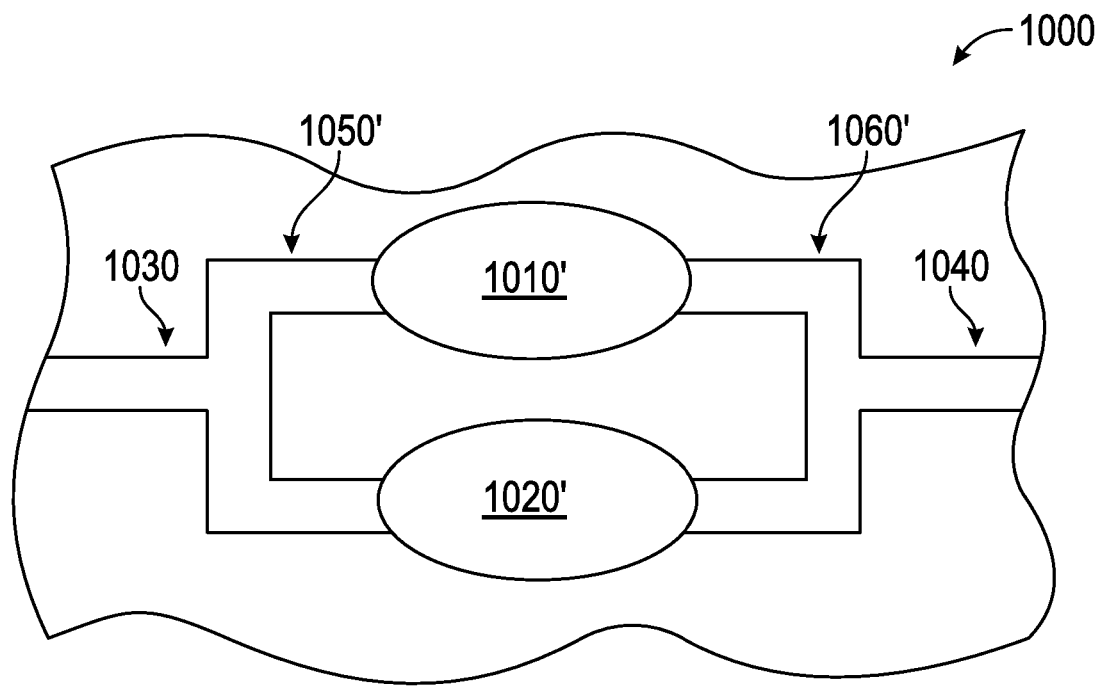

FIGS. 7A-7B shows an array 1000 of pump assemblies (such as any of the pump assemblies disclosed above). Though FIGS. 7A-7B show an array 1000 with two pump assemblies, one of skill in the art will recognize that the array 1000 can have more than two pump assemblies.

FIG. 7A shows a first pump assembly 1010 and a second pump assembly 1020 arranged in series between an inlet portion 1030 and an outlet portion 1040, the pump assemblies 1010, 1020 interconnected by an intermediate portion 1050. Arranging the pump assemblies 1010, 1020 in series advantageously allows for the array 1000 to have an increased pressure capability. In one embodiment, the first and second pump assemblies 1010, 1020 can operate in anti-phase to each other to reinforce fluid movement between the assemblies.

FIG. 7B shows a first pump assembly 1010' and a second pump assembly 1020' arranged in parallel between an inlet portion 1030 and an outlet portion 1040. The inlet portion 1030 is in fluid communication with the pump assemblies 1010', 1020' via an inlet manifold 1050', and the outlet portion 1040 is in fluid communication with the pump assemblies 1010', 1020' via an outlet manifold 1060'. Arranging the pump assemblies 1010', 1020' in parallel advantageously allows the array 1000 to generate an increased flow rate therethrough. In one embodiment, the first and second pump assemblies 1010', 1020' can operate in phase relative to each other to effect fluid movement through the array 1000.

Figure 8:
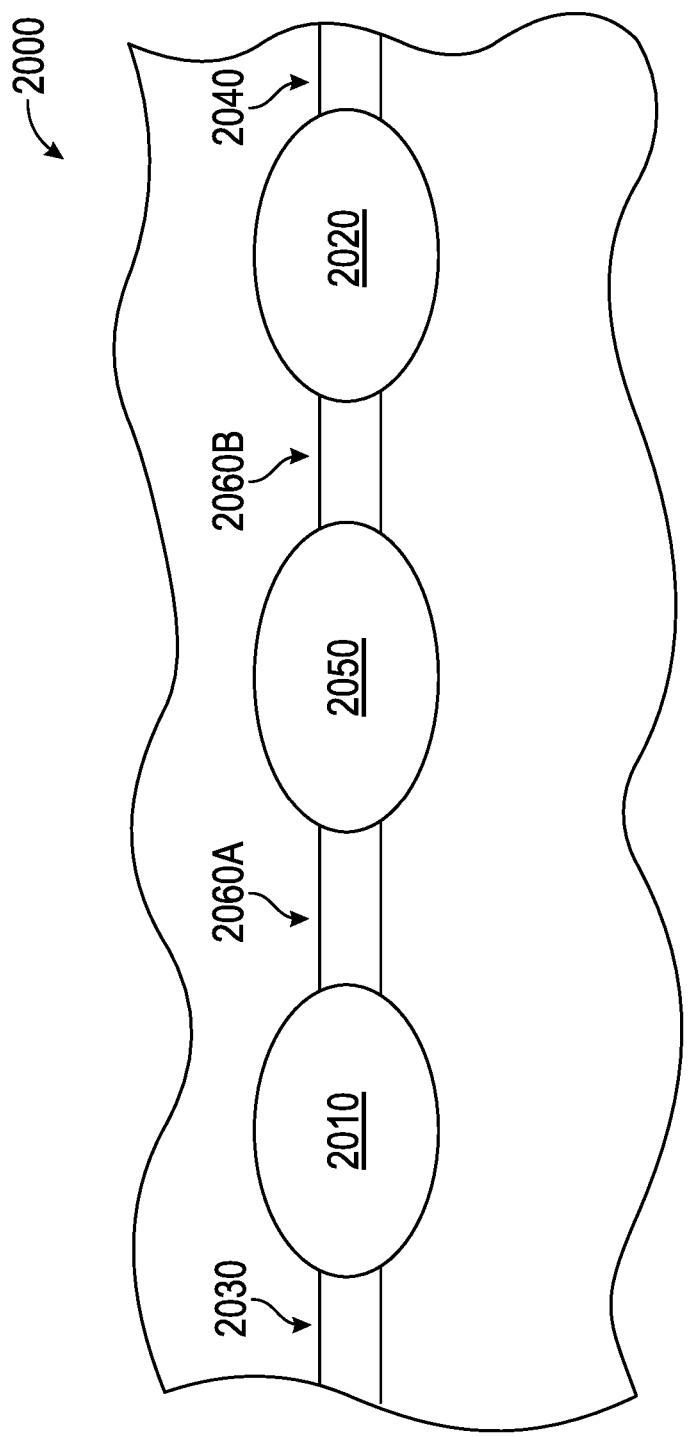
FIG. 8 shows a schematic top view of an array including pump assemblies.

FIG. 8 shows another embodiment of an array 2000 that includes two or more pump assemblies (such as any of the pump assemblies disclosed above).

In the illustrated embodiment, the array 2000 has a first pump assembly 2010 and a second pump assembly 2020 disposed between an inlet portion 2030 and an outlet portion 2040 of the array 2000. A chamber 2050 is interposed between the pump assemblies 2010, 2020 and interconnected via passages 2060A, 2060B with the pump assemblies 2010, 2020. The chamber 2050 does not have magnets or electromagnets therein, and can serve as a pressure or vacuum accumulator and/or to smooth flow through the array 2000. Though FIG. 8 shows an array 2000 with two pump assemblies and one accumulator chamber, one of skill in the art will recognize that the array 2000 can have more than two pump assemblies and a plurality of accumulator chambers.

Figure 9:
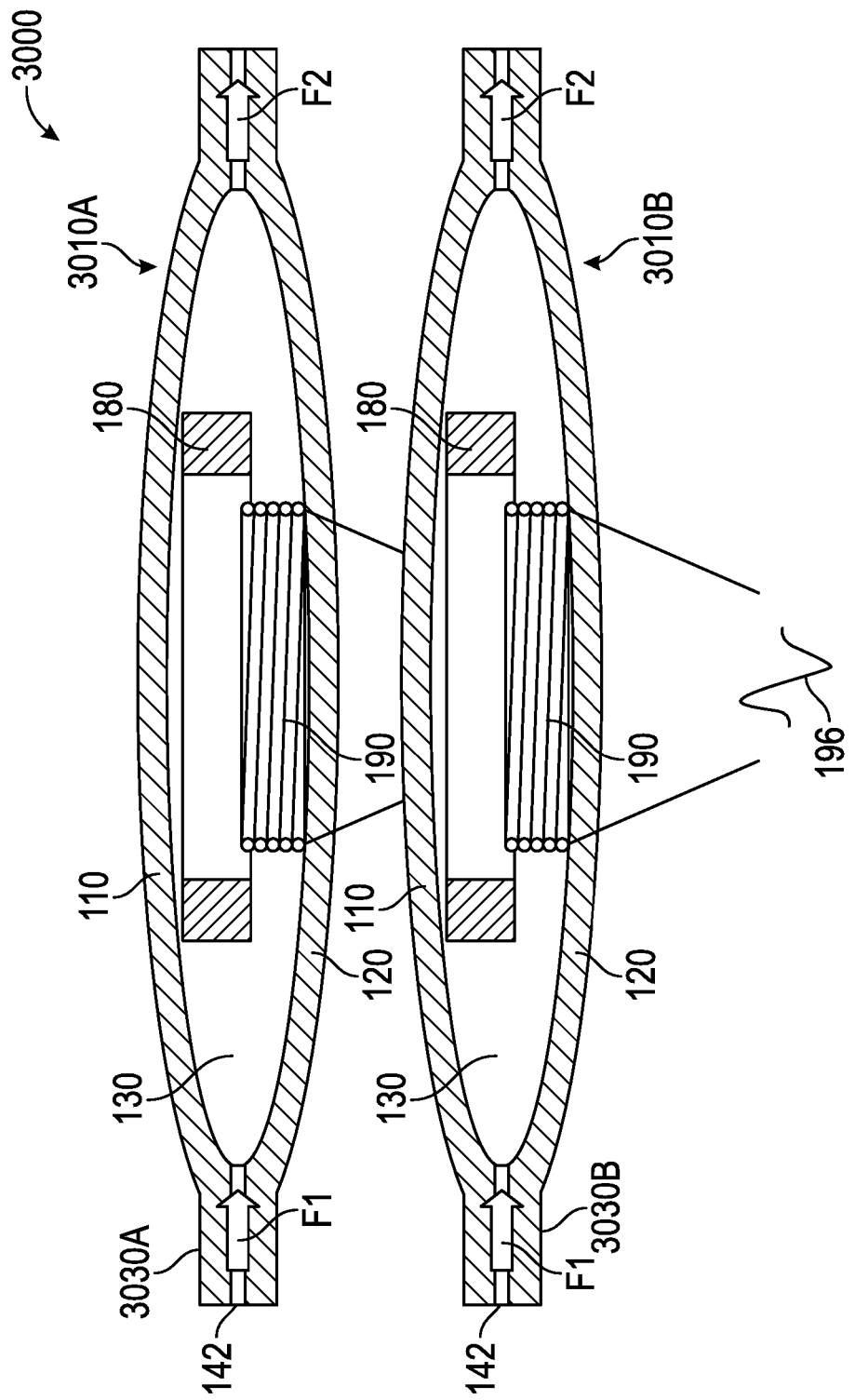
FIG. 9 shows a schematic top view of a pump system including pump assemblies.

FIG. 9 shows another embodiment of a pump system 3000 that includes two or more pump assemblies (such as any of the pump assemblies disclosed above). The pump system 3000 has a first pump assembly 3010A and a second pump assembly 3010B arranged one over the other in separate layers. The first and second pump assemblies 310A, 310B extend between inlet portions 3030A, 3030B and outlet portions 3040A, 3040B, respectively. The first and second pump assemblies 3010A, 3010B are operated in anti-phase so that the common wall or membrane between the assemblies 3010A, 3010B is driven by the electromagnetic elements in both assemblies 3010A, 3010B.

Figure 10:
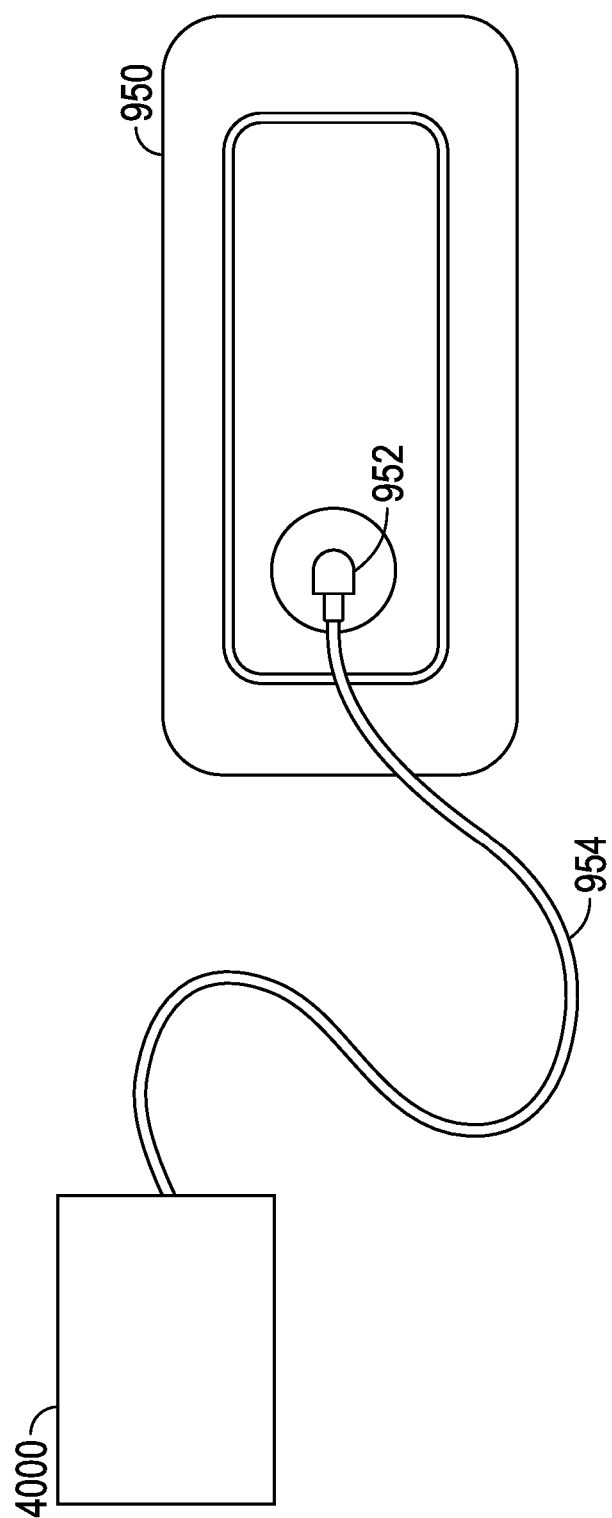
FIG. 10 shows a schematic top view of a pump system in fluid communication with a wound dressing.

FIG. 10 shows a pump system 4000 in fluid communication with a wound dressing 950 via a conduit 954 that connects to a port 952 on the dressing 950. The pump system 4000 can include one or more pump assemblies (such as the pump assemblies disclosed above). In some embodiments, the pump system 4000 includes an array (such as one of the arrays disclosed above). In some embodiments, the pump system 4000 can be configured to operate in a canisterless system, in which the wound dressing, such as wound dressing 950, retains exudate aspirated from the wound. Such a dressing can include a filter, such as a hydrophobic filter, that prevents passage of liquids downstream of the dressing (toward the pump system). In other embodiments, the pump system can be configured to operate in a system having a canister for storing at least part of exudate aspirated from the wound. Such canister can include a filter, such as a hydrophobic filter, that prevents passage of liquids downstream of the dressing (toward the pump system). In yet other embodiments, both the dressing and the canister can include filters that prevent passage of liquids downstream of the dressing and the canister. The dressing 950 can include one or more layer of woven, non-woven foam or superabsorbent layer, or a combination thereof.

Figure 11A:
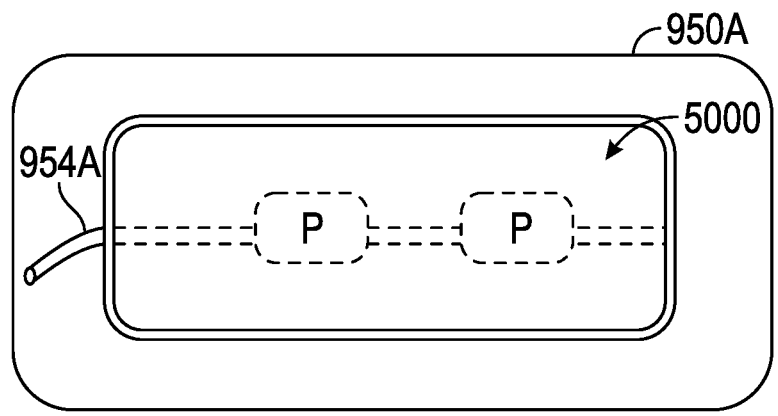
FIG. 11A show a schematic top view of a wound dressing with a pump system.

FIG. 11A shows one embodiment of a dressing 950A with a pump system 5000 in fluid communication with the dressing 950A via a conduit 954A. The pump system 5000 can be coupled to the dressing 950A, for example via an adhesive) so that the pump system 5000 is disposed on the dressing 950A. The pump system 5000 can include one or more pump assemblies P (such as the pump assemblies disclosed above). In some embodiments, the pump system 5000 includes an array (such as one of the arrays disclosed above). The dressing 950A can include one or more layer of woven, non-woven foam or superabsorbent layer, or a combination thereof.

Figure 11B:
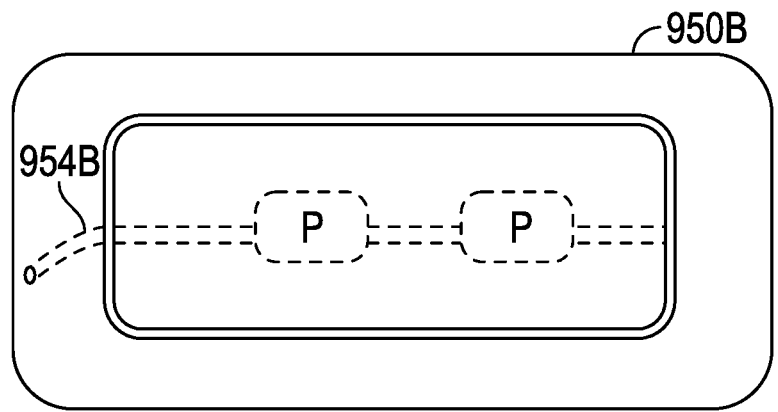
FIG. 11B show a schematic top view of a wound dressing with a pump system.

FIG. 11B shows another embodiment of a dressing assembly 950B with a pump system 6000 incorporated into the dressing assembly 950B. An internal conduit 954B can fluidly interconnect the pump system 6000 with the wound site (e.g., via one or more layers of the dressing 950B). The pump system 6000 can include one or more pump assemblies P (such as the pump assemblies disclosed above). In some embodiments, the pump system 6000 includes an array (such as one of the arrays disclosed above). The dressing 950B can include one or more layer of woven, non-woven foam or superabsorbent layer, or a combination thereof.

The magnets disclosed herein, such as the magnet (e.g., magnet 180, 280, etc.) can be made of any suitable material, such as mild steel, a sintered soft magnetic metal such as GKN 72-IBP2 (S-FeP-130), or sintered steel (or any suitable magnetic or ferromagnetic material). The magnet can be made from Neodymium-Iron-Boron (NdFeB)—N 45 M, Neodymium N33, or any other suitable material magnetic material. This material can be used to maximize field strength and minimize losses, thereby increasing the efficiency of the pump unit (e.g., pump assembly 100).

The pump assembly designs disclosed herein, whether provided as a single unit or in as part of an array (such as the arrays described above), provide various advantages. For example, such pump assemblies are flexible and therefore do not generate pressure points if lain upon (for example if the pump assembly is attached to, or incorporated in, a wound dressing assembly). Additionally, the pump assemblies disclosed herein are smaller and simpler to assemble than existing drum pumps. Further, when provided as part of a wound dressing (e.g., whether attached to or integrally formed with the wound dressing), the pump assemblies can be scalable with the dressing size, allowing the size of the array to be adjusted along with the size of the wound dressing, and thereby have a lower unit cost than existing pump assemblies. Still another advantage of the pump assemblies disclosed herein is that their structure can allow for smaller gaps between the magnetic actuators (e.g., smaller gap between the magnet 180 and electromagnet 190 in FIG. 1), thereby increasing the efficiency of the pump assembly.

Figure 12A:
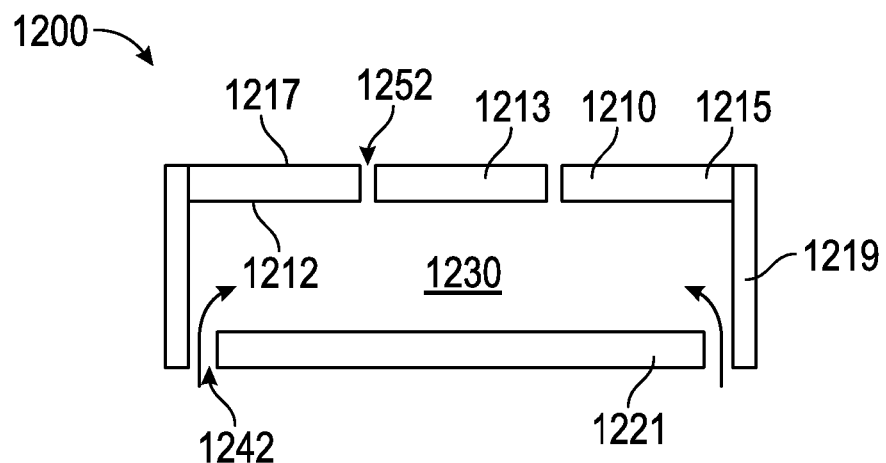
FIGS. 12A-C show a schematic cross-sectional side view of a pump assembly.
Figure 12B:
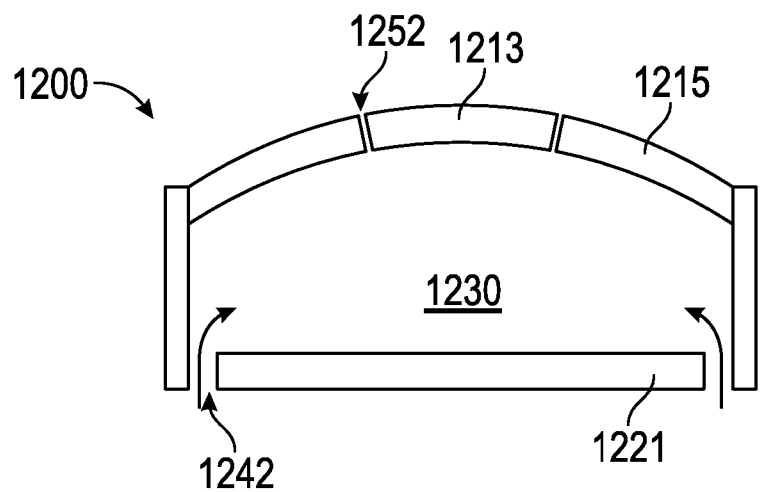
Figure 12C:
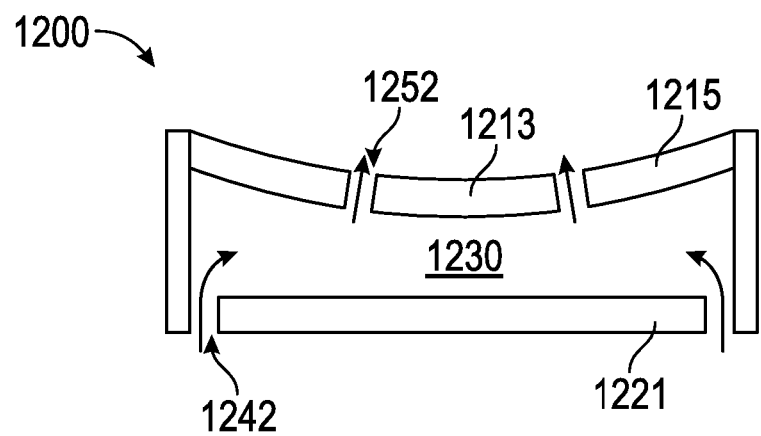

FIGS. 12A-C show cross-sectional views of an embodiment of the pump assembly where the valving and/or pumping action of the pump assembly is achieved using one or more materials that change shape when exposed to an electrical potential. Examples of suitable materials include but are not limited to liquid crystals and piezoelectric crystals (e.g., lead zirconate titanate (PZT)). For the sake of clarity, a material that changes shape when exposed to an electrical potential will hereinafter be referred to as PZT; however, as mentioned, other suitable materials can be used in place of or in addition to PZT.

The pump assembly 1200 is similar to the pump assembly 100 shown in FIG. 1, except as noted below. Thus, the reference numerals used to designate the various components of the pump assembly 1200 are identical to those used for identifying the corresponding components of the pump assembly 100 in FIG. 1, except that the reference numerals of the pump assembly 1200 begin with a "12". Therefore the description for the various components of the pump assembly 100 shown in FIG. 1 is understood to apply to the corresponding components of the pump assembly 1200 in FIGS. 12A-C, except as described below.

In the illustrated embodiment, the pump assembly 1200 has a first membrane 1210 that can move relative to an anchor surface 1221. FIG. 12A shows the first membrane 1210 in a default position. FIG. 12B shows the first membrane 1210 in a position that is deflected away from the anchor surface 1221. FIG. 12C shows the first membrane 1210 deflected toward the anchor surface 1221. The first membrane 1210 and the anchor surface 1221 can define a chamber 1230 therebetween. The chamber 1230 is surrounded by a sidewall 1219. Optionally, the sidewall 1219 and the anchor surface 1221 are rigid so that the volume changes in the chamber 1230 are due to movement of the first membrane 1210 alone and not from movement of the anchor surface 1221 or sidewall 1219.

The pump assembly 1200 can have an inlet passage 1242 that provides a path for fluid (e.g. air) to enter the chamber 1230. The pump assembly 1200 can have an outlet passage 1252 that provides a path for fluid to exit the chamber 1230. In the illustrated embodiment, the outlet passage 1252 is interposed between a central portion 1213 and a lateral portion 1215 of the first membrane 1210. The central portion 1213 and/or the lateral portion 1215 of the first membrane 1210 can include PZT. As discussed below, the pump assembly 1200 can be adapted in a number of ways to achieve the desired movement of the first membrane 1210. For example, PZT can be mounted on the inner surface 1212 of the first membrane 1210 and arranged so that when the PZT swells in a radial direction the first membrane 1210 moves away from the anchor surface 1221. Additionally or alternatively, PZT can be mounted on the outer surface 1217 of the first membrane 1210 and arranged so that when the PZT swells in a radial direction the first membrane 1210 moves toward the anchor surface 1221. If PZT is used on both the inner and outer surfaces 1212, 1217 of the first membrane 1210, the PZT on the inner surface 1212 can be energized out of phase with the PZT on the outer surface 1217.

FIG. 12B shows the pump assembly 1200 in the intake position, which lets air into the chamber 1230. As shown in FIG. 12B, as the first membrane 1210 moves away from the anchor surface 1221, the central portion 1213 and lateral portion 1215 of the first membrane 1210 approach one another, thereby narrowing the outlet passage 1252 and reducing airflow through the outlet passage 1252. The movement of the first membrane 1210 away from the anchor surface 1221 causes the chamber 1230 to expand, which draws air into the chamber 1230 through the inlet passage 1242. FIG. 12C shows the pump assembly 1200 in the exhaust position, which lets air out of the chamber 1230. As shown in FIG. 12C, when the first membrane 1210 moves toward the anchor surface 1221, the central portion 1213 and lateral portion 1215 of the first membrane 1210 to move away from one another, thereby allowing air to pass more easily through the outlet passage 1252. As discussed in more detail below, the inlet and outlet passages 1242, 1252 can be tapered or otherwise adapted so that air passes through the passages 1242, 1252 more easily in a first direction than in an opposite direction. In this way, the inlet and outlet passages 1242, 1252 can be adapted so that air preferentially flows through the outlet passage 1252 and not the inlet passage 1242 as the first membrane 1210 approaches the anchor surface 1221.

Figure 12D:
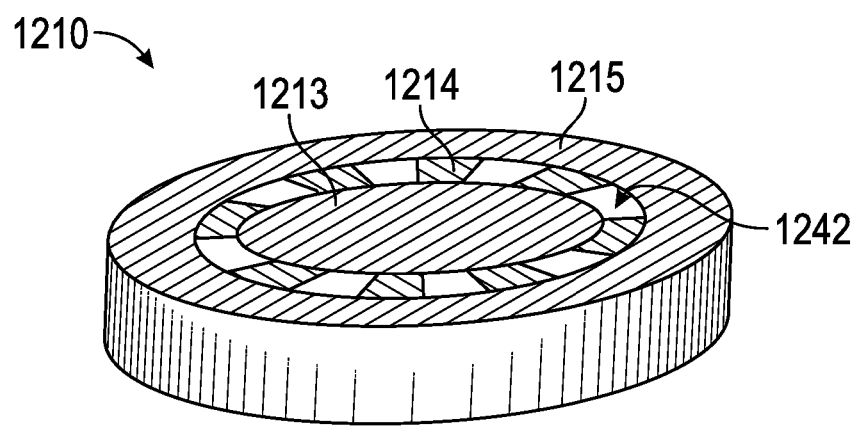
FIG. 12D shows a schematic perspective view of a membrane of a pump system.

FIG. 12D is a perspective view of an embodiment of the first membrane 1210 of the pump assembly 1200. A plurality of connectors 1214 join the central portion 1213 of the first membrane 1210 to the lateral portion 1215 of the first membrane 1210. In some embodiments, the connectors 1214 include an elastomeric material. In certain variants, the central portion 1213 is PZT, the lateral portion 1215 is PZT, and the connectors 1214 are elastomeric. In some embodiments, the central portion 1213 does not include PZT and is a rigid solid that does not substantially deform as the first membrane 1210 moves between the intake and exhaust positions. For the sake of clarity, a material that does not include PZT and does not substantially deform as the pump assembly moves from the intake to exhaust position will hereinafter be referred to as "solid". In some embodiments, the central portion 1213 is solid, the connectors 1214 are elastomeric, and the lateral portion 1215 is PZT. In certain variants, the central portion 1213 is PZT, the connectors 1214 are elastomeric, and the lateral portion 1215 is solid. In some embodiments, the central portion 1213 is bi-stable. Bi-stable refers to the central portion buckling between the intake and exhaust positions while not being stable in intervening positions between the intake and exhaust positions. In some variants, the central portion 1213 is bi-stable, the connectors 1214 are PZT, and the lateral portion 1215 is PZT. In certain variants, the central portion 1213, the connectors 1214, and the lateral portion 1215 are each PZT.

Figure 13:
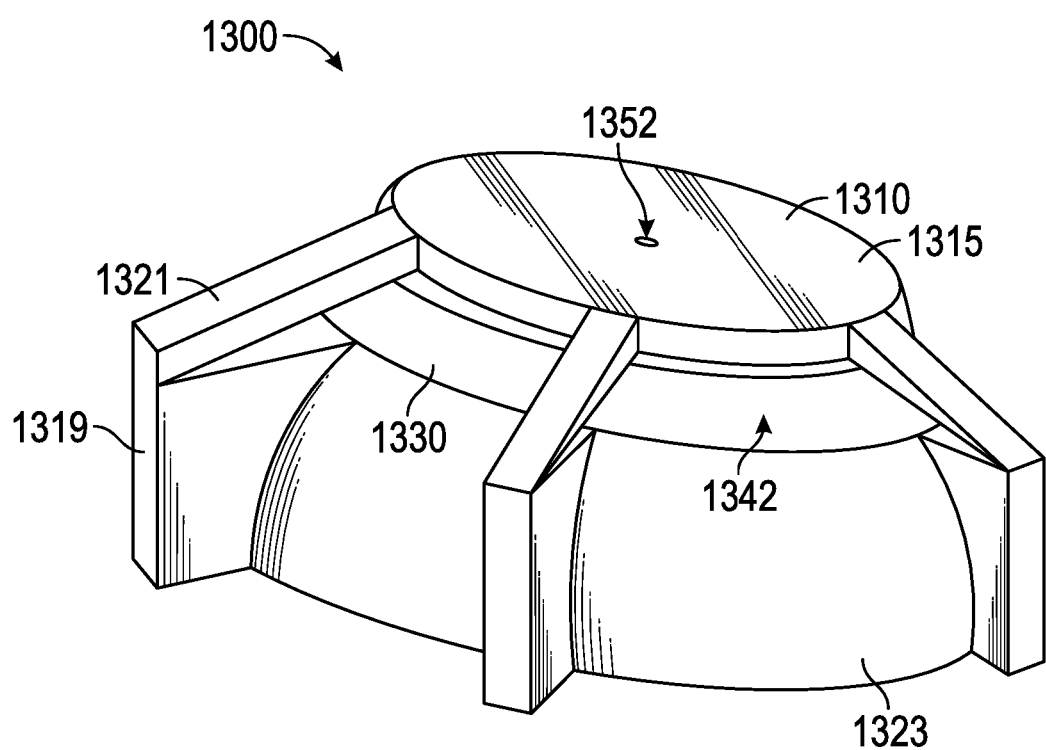
FIG. 13 shows a schematic perspective view of a pump assembly.

FIG. 13 shows a perspective view of an embodiment of the pump assembly. The pump assembly 1300 is similar to the pump assembly 100 shown in FIG. 1, except as noted below. Thus, the reference numerals used to designate the various components of the pump assembly 1300 are identical to those used for identifying the corresponding components of the pump assembly 100 in FIG. 1, except that the reference numerals of the pump assembly 1300 begin with a "13". Therefore the description for the various components of the pump assembly 100 shown in FIG. 1 is understood to apply to the corresponding components of the pump assembly 1300 in FIG. 13, except as described below.

The first membrane 1310 has an outlet passage 1352 that is surrounded by the lateral portion 1315 of the first membrane 1310. The outlet passage 1352 opens and closes as the lateral portions 1315 extend radially outward and inward. The pump assembly 1300 has a sidewall 1319 that surrounds the chamber 1330. The lateral portion 1315 has an arm 1321 that connects the first membrane 1310 to the sidewall 1319. In the illustrated embodiment, the pump assembly 1300 is shown in the intake position, in which the first membrane 1310 is dome-shaped with the surface of the first membrane 1310 that faces the chamber 1330 having a concave shape. Air flows into the chamber 1330 through inlet passages 1342 interposed between the arms 1321 of the first membrane 1310. The entry portion 1323 of the sidewall 1319 can have a swept path geometry that facilitates air flow along the entry portion 1323 and into the chamber 1330. In the illustrated embodiment, the pump assembly 1300 is in the intake position and the outlet passage 1352 has narrowed so that substantially no air flows through the outlet passage 1352. As discussed below, valving of the pump assembly can be achieved by energizing the PZT of the lateral portion 1315 and the arm 1321 at a slightly different times. For example, the lateral portion 1315 can be energized ahead of the arm 1321 to close the outlet passage 1352 before deflecting the first membrane 1310 so that air is drawn into the chamber 1330 through the inlet passage 1342 and not through the outlet passage 1352.

Figure 14A:
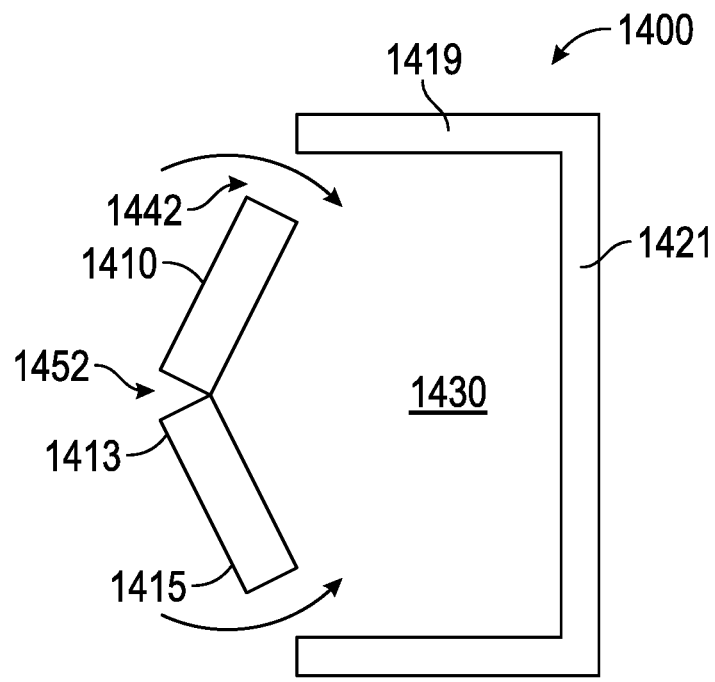
FIGS. 14A-B show a schematic cross-sectional side view of a pump assembly.
Figure 14B:
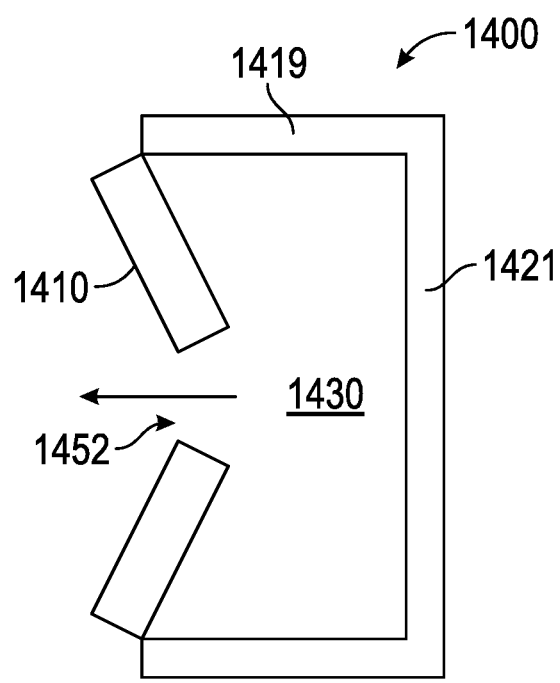

FIGS. 14A-B show a cross-sectional view of another embodiment of the pump assembly. The pump assembly 1400 is similar to the pump assembly 100 shown in FIG. 1, except as noted below. Thus, the reference numerals used to designate the various components of the pump assembly 1400 are identical to those used for identifying the corresponding components of the pump assembly 100 in FIG. 1, except that the reference numerals of the pump assembly 1400 begin with a "14". Therefore the description for the various components of the pump assembly 100 shown in FIG. 1 is understood to apply to the corresponding components of the pump assembly 1400 in FIGS. 14A-B, except as described below.

FIG. 14A shows the pump assembly 1400 in the intake position, with air entering the chamber 1430 through the inlet passages 1442. FIG. 14B shows the pump assembly 1400 in the exhaust position, with air exiting the chamber 1430 through the outlet passage 1452. Although not shown, the pump assembly 1400 would include an inlet and outlet manifold system that channels air flow through the inlet passage 1442, then through the chamber 1430, and finally through the outlet passage 1452. In other words, the manifold system (not shown) would be adapted to prevent air from crossing between the inlet and outlet passages 1442, 1452 without passing through the chamber 1430.

In the intake position of the embodiment shown in FIG. 14A, the lateral portions 1415 of the first membrane 1410 move radially inward from the sidewall 1419 to open the inlet passage 1442. At the same time, the central portion 1413 of the first membrane 1410 moves radially inward and away from the anchor surface 1421, thereby closing the outlet passage 1452 and expanding the volume of the chamber 1430. In the exhaust position (FIG. 14B), the lateral portions 1415 move radially outward toward the sidewall 1419 to close the inlet passage 1442. At the same time, the central portion 1413 of the first membrane 1410 moves radially outward and toward the anchor surface 1421 of the chamber 1430, thereby opening the outlet passage 1452 and reducing the volume of the chamber 1430.

Figure 15A:
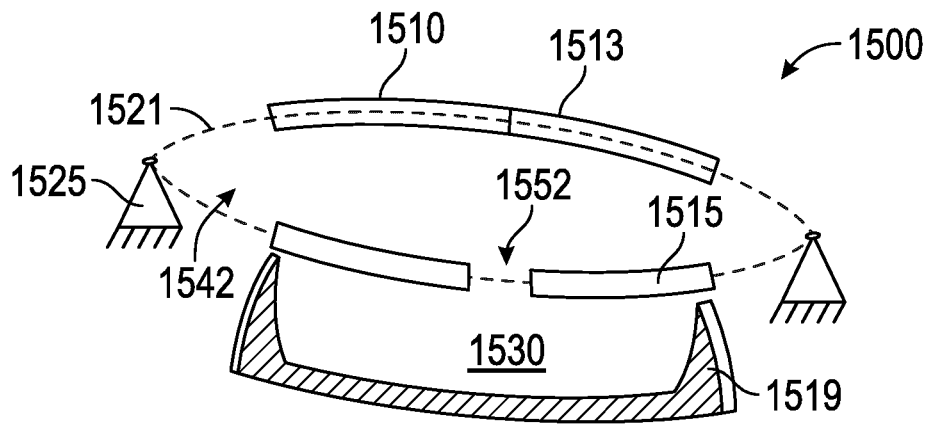
FIG. 15A shows a schematic cross-sectional side view of a pump assembly.
Figure 15B:
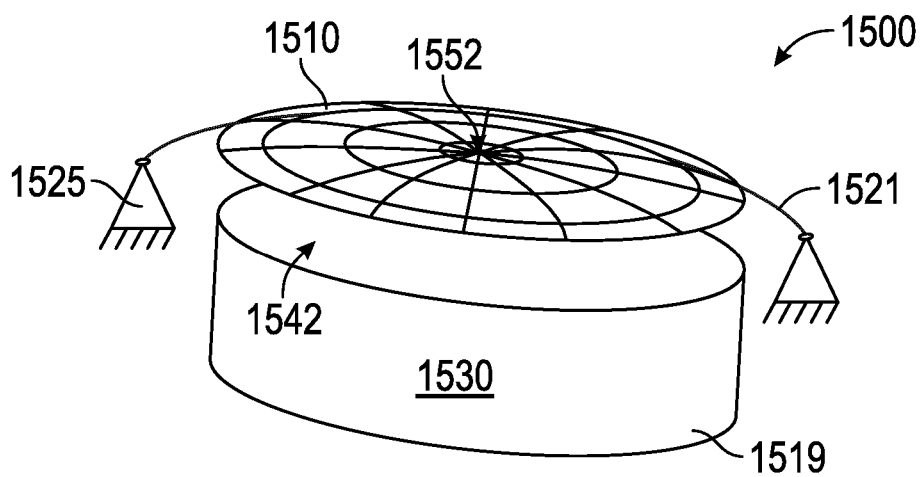
FIG. 15B shows a schematic perspective view of a pump assembly.
Figure 15C:
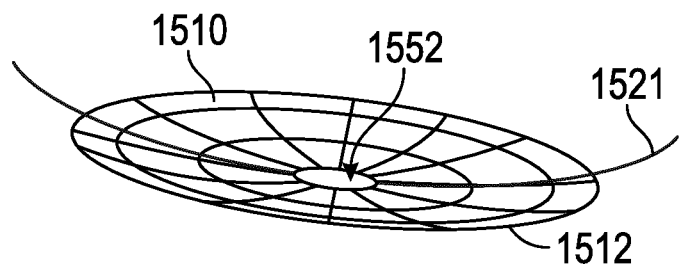
FIG. 15C shows a perspective view of a membrane of a pump assembly.

FIGS. 15A-C show a cross-sectional view of another embodiment of the pump assembly. The pump assembly 1500 is similar to the pump assembly 100 shown in FIG. 1, except as noted below. Thus, the reference numerals used to designate the various components of the pump assembly 1500 are identical to those used for identifying the corresponding components of the pump assembly 100 in FIG. 1, except that the reference numerals of the pump assembly 1500 begin with a "15". Therefore the description for the various components of the pump assembly 100 shown in FIG. 1 is understood to apply to the corresponding components of the pump assembly 1500 in FIGS. 15A-C, except as described below.

FIG. 15A shows superposition of the first membrane 1510 in the intake and exhaust positions. The first membrane 1510 is shaded white in the intake position and shaded black in the exhaust position. The lateral portion 1515 has an arm 1521 that connects the first membrane 1510 to a ring mount 1525. The arms 1521 can include PZT material. In some embodiments, the arms 1521 do not include PZT material. In certain embodiments, the arms 1521 and/or the first membrane 1510 can be bi-stable, i.e., buckling between a convex or concave position while not being stable in a flat orientation. In the intake position, the inlet passage 1542 opens to allow air to enter the chamber 1530. In the exhaust position, the arm 1521 seals the inlet passage 1542 while the central portion 1513 of the first membrane opens the outlet passage 1552, allowing air within the chamber 1530 to pass to the outlet manifold (not shown) of the pump assembly 1500.

FIG. 15B is a perspective view of an embodiment of the pump assembly 1500 in the intake position. In the illustrated embodiment, the inlet passage 1542 opens to connect to the chamber 1530 through a gap formed when the first membrane 1510 moves longitudinally away from the sidewall 1519. At the same time, the outlet passage 1552 is sealed by the central portions 1513 of the first membrane 1510 expanding radially inward. FIG. 15C is a perspective view of the first membrane 1510 in the exhaust position, showing that the outlet passage 1552 opens when the inner surface 1512 of the first membrane 1510 becomes convex.

Figure 16A:
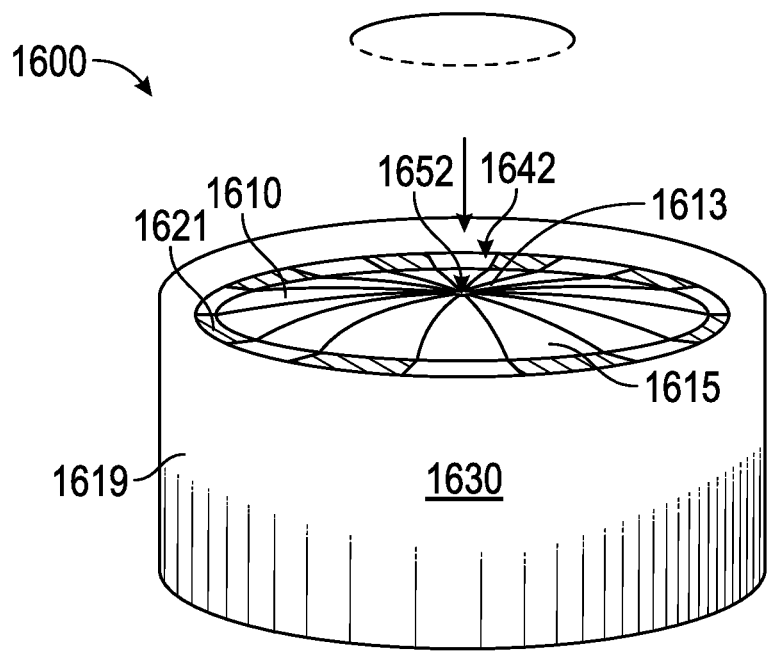
FIGS. 16A-B show a schematic perspective view of a pump assembly.
Figure 16B:
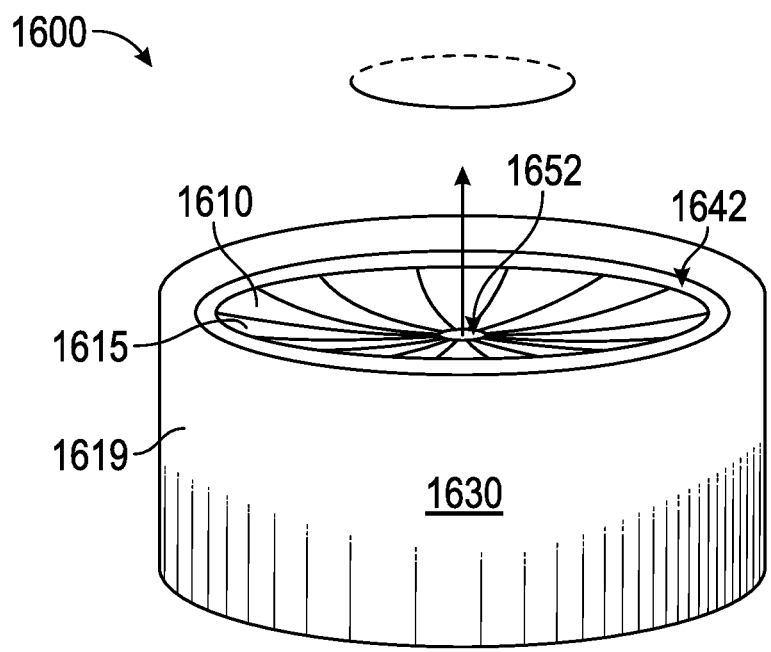

FIGS. 16A-B show a perspective view of another embodiment of the pump assembly. The pump assembly 1600 is similar to the pump assembly 100 shown in FIG. 1, except as noted below. Thus, the reference numerals used to designate the various components of the pump assembly 1600 are identical to those used for identifying the corresponding components of the pump assembly 100 in FIG. 1, except that the reference numerals of the pump assembly 1600 begin with a "16". Therefore the description for the various components of the pump assembly 100 shown in FIG. 1 is understood to apply to the corresponding components of the pump assembly 1600 in FIGS. 16A-B, except as described below.

FIG. 16A is a perspective view of an embodiment of the pump assembly 1600 in the intake position. In the illustrated embodiment, the central portion 1613 of the first membrane 1610 moves radially inward to seal the outlet passage 1652. The central portion 1613 also moves longitudinally away from the ring mount 1619, thereby giving the top surface of the first membrane 1610 a convex shape. At the same time, the lateral portion 1615 of the first membrane 1610 moves radially inward, opening the inlet passage 1642 to allow air to enter the chamber 1630 through an annular gap that is formed between the ring mount 1619 and the lateral portion 1615 of the first membrane 1610. In some embodiments, the inlet passages 1642 may occupy about 5% of the area of the annular gap between the lateral portion 1615 and the ring mount 1619 with the arms 1621 occupying the remainder of the annular gap. However, in other embodiments, the inlet passages 1642 may occupy more or less than 5% of the area of the annular gap between the lateral portion 1615 and the ring mount 1619.

FIG. 16B is a perspective view of the embodiment of the pump assembly 1600 in the exhaust position. The first membrane 1610 bends into the chamber, giving the top surface of the first membrane 1610 a concave shape. The central portion 1613 of the first membrane moves radially outward, thereby enlarging the outlet passage 1652 and allowing air to flow out of the chamber 1630 through the outlet passage 1652.

Figure 17A:
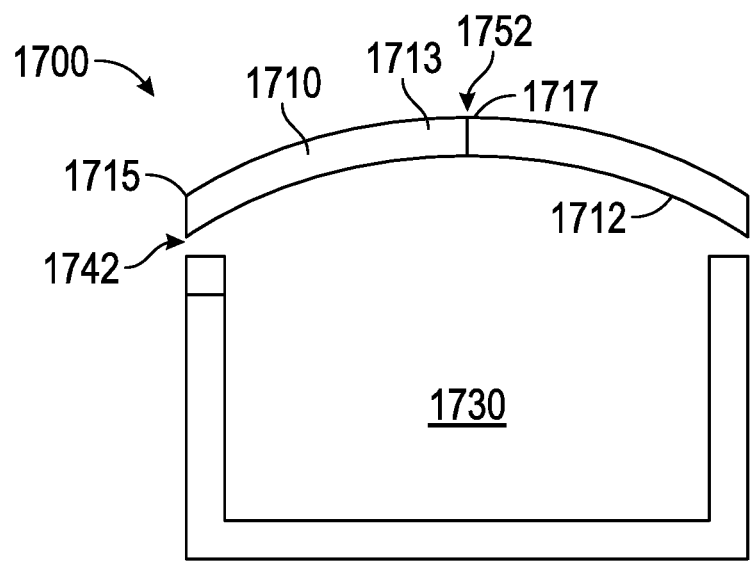
FIGS. 17A-B show a schematic cross-sectional side view of a pump assembly.
Figure 17B:
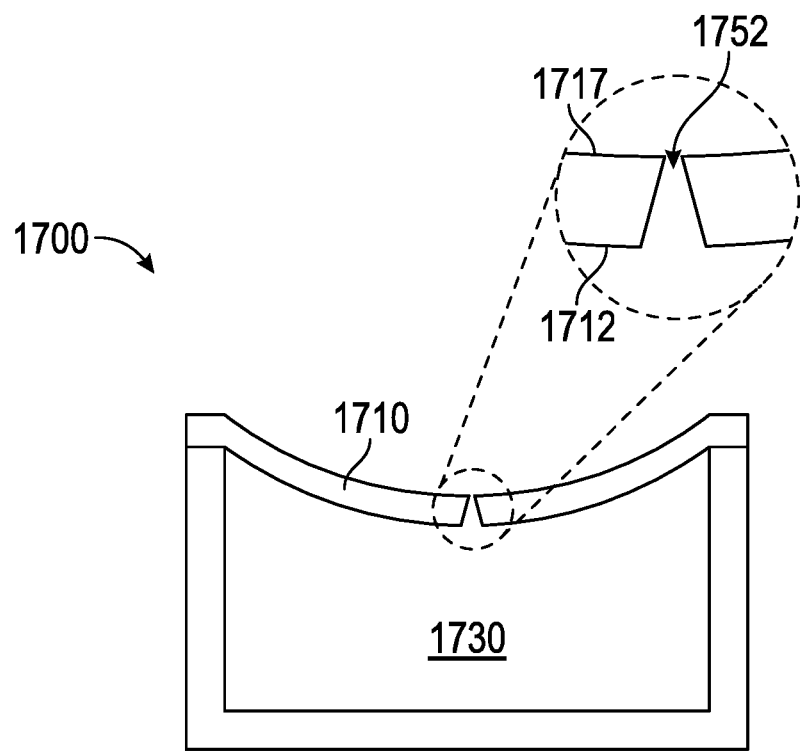

FIGS. 17A-B illustrate features of the inlet and outlet passages 1742, 1752 of the pump assembly. The pump assembly 1700 is similar to the pump assembly 100 shown in FIG. 1, except as noted below. Thus, the reference numerals used to designate the various components of the pump assembly 1700 are identical to those used for identifying the corresponding components of the pump assembly 100 in FIG. 1, except that the reference numerals of the pump assembly 1700 begin with a "17". Therefore the description for the various components of the pump assembly 100 shown in FIG. 1 is understood to apply to the corresponding components of the pump assembly 1700 in FIGS. 17A-B, except as described below.

FIG. 17A shows the pump assembly 1700 in the intake configuration. The PZT material of the first membrane 1710 can be energized at a frequency of about 16 kHz, causing the first membrane 1710 to oscillate between the intake and exhaust positions at the same frequency. In some embodiments, the PZT material of the first membrane is energized at about: 16 kHz, 20 kHz, 40 kHz, 80 kHz, and frequencies therebetween. The primary frequencies for energizing the PZT will be within the range from about 18 kHz to about 24 kHz. Smaller PZT membranes will generally run higher because natural frequency is a function of size and aspect ratio. Smaller size and greater thickness will raise the frequency. In certain embodiments, the PZT valves run at a lower frequency than the PZT membrane. The energizing frequency can be selected to avoid audible frequencies. The highest normal hearing frequency is about 24 kHz in youth, lowering to about 18 kHz in the middle aged. Higher frequencies are therefore inaudible and therefore apparently silent. The rapid movement of the first membrane 1710 can cause the air flow through the inlet and outlet passages 1742, 1752 to have a high Reynolds number (Re). In some embodiments, the narrowing of the outlet passage 1752 and the rapid movement of the first membrane 1710 causes the airflow through the outlet passage 1752 to have Re>1,000. In some embodiments, the Re of the peak air flow through the outlet passage 1752 is about: 500; 1,000; 2,000; 4,000; and values therebetween. The flow can optionally be moderately sinusoidal and can therefore have a variable Reynolds number with time. The lowest peak in Reynolds number would be expected to be around 150, with the highest around 6000. In certain embodiments, the PZT valving allows a lower peak velocity for the same overall flow rate, reducing the back pressure.

Referring to FIG. 17A, the pump assembly 1700 can be adapted so that the outlet passage 1752 behaves as effectively closed even though the central portions 1713 do not actually contact one another. It can be advantageous to avoid complete closure of the outlet passage 1752 to avoid the central portions 1713 contacting one another and generating shockwaves. Shockwaves compromise pump efficiency and can cause pump elements to wear out. A "closing ratio" can be defined as the ratio between the cross-sectional area of the outlet passage 1752 at the intake position and the cross-sectional area of the outlet passage 1752 at the exhaust position. In some embodiments, the closing ratio is about: 0.8, 0.5, 0.3, 0.1, 0.03, and values therebetween. In certain variants, a maximum closing ratio of about 0.5 can optionally be used. In some geometries, a closing ratio of 0.8 provides a measurable improvement in restricting air flow through the outlet passage 1752 in the intake position. In some embodiments, the cross-sectional area of the outlet passage 1752 in the intake position approaches a completely closed configuration such that no effective minimum closing ratio is provided. In many embodiments, a closing ratio 0.03 can optionally be selected as an acceptable minimum closing ratio as such a ratio avoids contact between the PZT elements while producing an overall size of the outlet passage 1752 in the intake position that will be very small at that point. In addition, utilizing a chamfered edge can improve the function of the outlet passage 1752 as a sharp edge can reduce the effective width of a small channel to 0.65 of the real width while a chamfer, or round, keeps it near to 1.0—therefore the chamfered edge can allow flow more easily in one direction than the other.

Referring to FIG. 17B, the first membrane 1710 can be adapted so that the outlet passage 1752 is tapered when the pump assembly 1700 is in the exhaust position. For example, the PZT can be mounted on the pump assembly 1700 so that the diameter of the outlet passage 1752 is wider at the bottom surface 1712 of the first membrane 1710 compared to the diameter of the outlet passage 1752 at the top surface 1717 of the first membrane 1710. Air will flow more easily out of the chamber 1730 than into it when the outlet passage 1752 is tapered as shown in the insert portion of FIG. 17B. Because air flow is impeded by sharp corners, the corners of the outlet passage 1752 can be rounded on the bottom surface 1712 of the first membrane 1710 and sharp on the top surface 1717 of the first membrane. The pump assembly 1700 can be adapted with similar features for the inlet passage 1742 to cause air to flow more easily into the chamber 1730 than out of the chamber 1730.

Figure 18A:
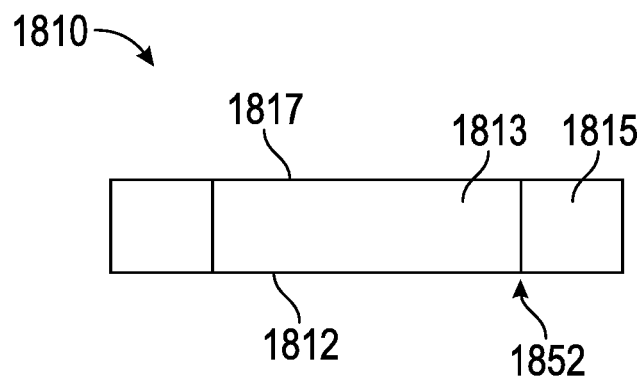
FIGS. 18A-B show a schematic cross-sectional side view of a membrane of a pump assembly.
Figure 18B:
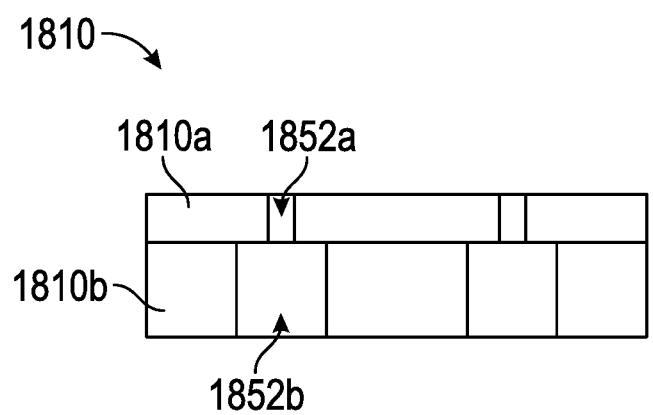

FIGS. 18A-B illustrate additional features of the outlet passage 1852 of the pump assembly. Referring to FIG. 18A, the first membrane 1810 can have a central portion 1813 that is surrounded by a lateral portion 1815, as previously described. The PZT can be mounted so that the central portion 1813 and lateral portion 1815 are closer to one another at the top surface 1817 of the first membrane 1810 compared to at the bottom surface 1812 of the first membrane 1810 when the first membrane 1810 is in the exhaust position. This will create a tapered outlet passage 1852 that favors air flow away from the chamber, as previously described.

FIG. 18B illustrates a layered first membrane 1810 that can be used to control air flow from the chamber. The first membrane 1810 has an upper layer 1810a that has an upper outlet portion 1852a that aligns with a lower outlet portion 1852b of the lower layer 1810b. The upper and lower layers 1810a,b can include PZT. The PZT in the upper layer 1810a can be energized slightly out of phase with the PZT in the lower layer 1810b to achieve valving of airflow to and from the chamber. The lower layer 1810b can be adapted to power the pumping action by driving the first membrane 1810 between the intake and exhaust positions. In some embodiments, the lower outlet portion 1852b has substantially the same cross-sectional area in the intake and exhaust positions with the upper outlet portion 1852a controlling airflow to and from the chamber. For example, when the first membrane 1810 is in the intake position, the PZT in the upper layer 1810a can be energized to open the upper outlet portion 1852a before the lower layer 1810b is energized to move the first membrane 1810 toward the exhaust position. After the upper outlet portion 1852a has opened partially or completely, the lower layer 1810b is energized to move the first membrane 1810 toward the exhaust position, allowing air to leave the chamber through the outlet passage 1852. When the first membrane 1810 is in the exhaust position, the upper layer 1810*a* can be energized to close the upper outlet portion 1852*a* before the lower layer 1810*b* is energized to move the first membrane 1810 toward the intake position. After the upper outlet portion 1852*b* has closed partially or completely, the lower layer 1810*b* is energized to move the first membrane 1810 toward the intake position, thereby preventing air from flowing into the chamber through the outlet passage 1852.

A "valve ratio" can be defined as the ratio between the cross-sectional area of the upper outlet portion 1852*a* to the cross-sectional area of the lower outlet portion 1852*b*. In some embodiments, the valve ratio of the pump assembly is about: 0.1, 0.2, 0.5, 0.8, 1.0, and values therebetween.

Figure 19A:
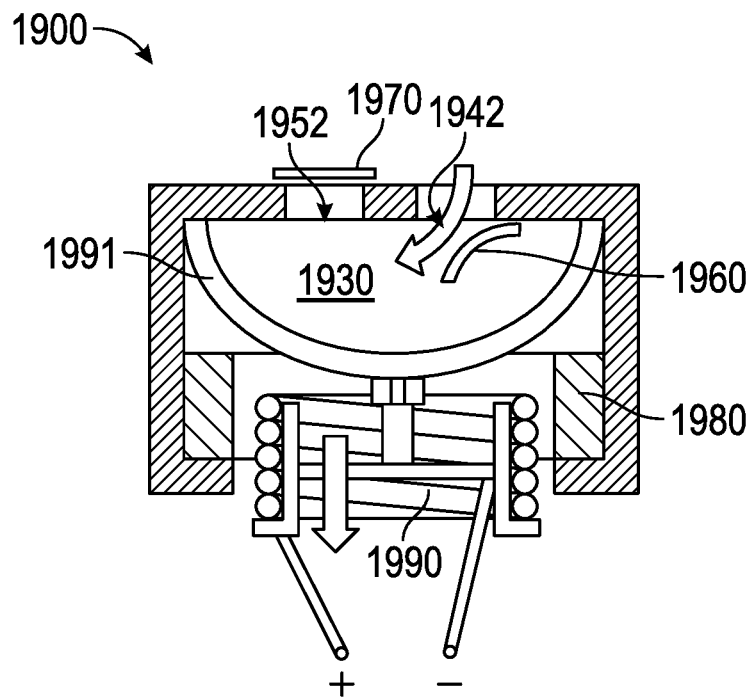
FIGS. 19A-B show a schematic cross-sectional side view of a membrane of a pump assembly.
Figure 19B:
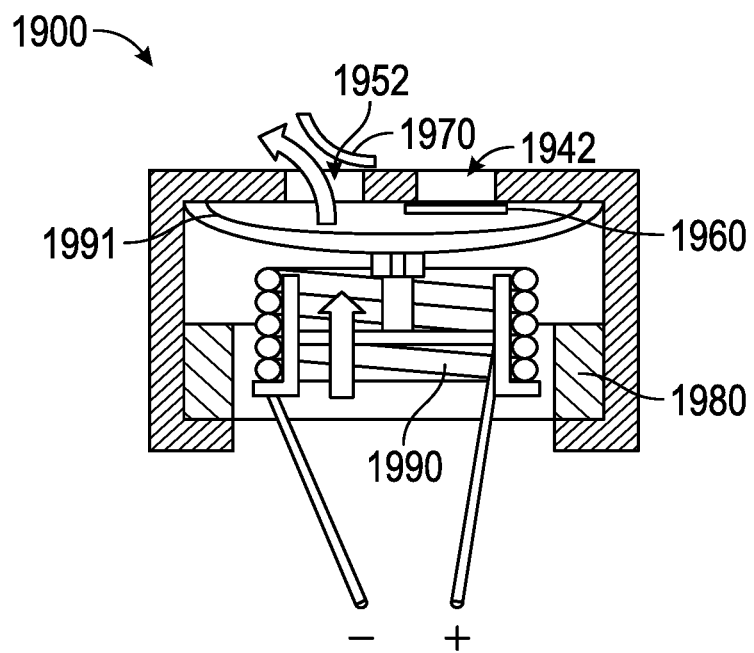

FIGS. 19A-B show a cross-sectional side view of a pump assembly. The pump assembly 1900 is similar to the pump assembly 100 shown in FIG. 1, except as noted below. Thus, the reference numerals used to designate the various components of the pump assembly 1900 are identical to those used for identifying the corresponding components of the pump assembly 100 in FIG. 1, except that the reference numerals of the pump assembly 1900 begin with a "19". Therefore the description for the various components of the pump assembly 100 shown in FIG. 1 is understood to apply to the corresponding components of the pump assembly 1900 in FIGS. 19A-B, except as described below.

The pump assembly 1900 includes a magnet 1980, an electromagnet 1990, and a diaphragm 1991. The electromagnet 1990 can optionally be a voice coil. In the illustrated embodiment, the diaphragm 1991 is connected to the electromagnet 1990 and moves with the electromagnet 1990 to expand and contract the volume of the chamber 1930 as electric current is delivered to the electromagnet 1990. The pump assembly 1900 has an inlet passage 1942 in fluid communication with the chamber 1930. The pump assembly 1900 has an outlet passage 1952 in fluid communication with the chamber 1930. A one-way valve 1960 allows fluid flow through the inlet passage 1942 into the chamber 1930 but inhibits (e.g., prevents) flow from the chamber 1930 into the inlet passage 1942 (e.g., inhibits reverse flow into the inlet passage 142). A one-way valve 1970 allows fluid flow from the chamber 1930 and through the outlet passage 1952 but inhibits (e.g., prevents) flow from the outlet passage 1952 into the chamber 1930 (e.g., inhibits reverse flow into the chamber 130). FIG. 19A shows the pump assembly 1900 in the intake position. FIG. 19B shows the pump assembly 1900 in the exhaust position.

The one-way valves 1960, 1970 can include PZT material and can be adapted to open and close in response to an applied electrical potential. In some embodiments, the piezo one-way valves 1960, 1970 are driven separately from the electromagnet 1990. In certain variants, the piezo one-way valves 1960, 1970 are driven by a square wave while the electromagnet 1990 is driven by a sine wave. In this way, the piezo one-way valves 1960, 1970 are effectively completely separate to the pump drive of the electromagnet 1990 and the diaphragm 1991. The piezo one-way valves 1960, 1970 can be configured to open when voltage is applied across each valve. In some embodiments, the valves are configured to close when no power is applied to the valve for lowest power consumption and leak rate. In some embodiments, the square wave that is used to control the piezo valves 1960, 1970 is in phase with the sine wave used to control the electromagnet 1990. In certain variants, however, the square wave might extend a little beyond to allow the outlet valve 1970 to close a little after the diaphragm 1991 has reached top dead center.

The square wave used to actuate the piezo one-way valves 1960, 1970 can be pulse width modulated and can operate with different drive frequencies. A benefit of using this valving system is that, for the cost of the power to drive the piezo valves 1960, 1970, the flow rate of the pump would increase. Additionally, the electromagnet 1990 could be driven at lower amplitudes for a given flow rate, which would be more efficient. It takes more energy to drive the pump at higher amplitudes due to increased strain of the diaphragm 1991. However, it requires a certain pressure difference to blow a non-return valve open, using potentially as much power as the rest of the pump assembly. As such, normal electromagnets 1990 are a trade-off between the amplitude necessary to blow the valve open and having the lowest stiction valves to avoid the valve leaking. A bigger amplitude makes the pneumatic efficiency higher but reduces the mechanical efficiency. This trade-off can be eliminated by controlling the valving to the chamber 1930 through piezo valves, in which case the valve power cost would be fixed, irrespective of amplitude of the pumping diaphragm 1991. Another benefit of independent piezo valving is that it allows a lower amplitude "over-square" pistons to work well. Over-square pistons are characterized generally by large diameter, small stroke, and high frequency operation. Such systems would be useful for bubble-drum pumping assemblies.

The PZT pump assemblies described in FIGS. 12A-19B can be incorporated into a wound dressing, as described in FIGS. 11A-B. For example, referring to FIG. 11A, a PZT pump assembly can be a pump system 5000 in fluid communication with the dressing 950A via a conduit 954A. As previously described, the pump system 5000 can be coupled to the dressing 950A, for example via an adhesive) so that the pump system 5000 is disposed on the dressing 950A. The pump system 5000 can include one or more pump assemblies P (such as the pump assemblies disclosed above). In some embodiments, the pump system 5000 includes an array (such as one of the arrays disclosed above). The dressing 950A can include one or more layer of woven, non-woven foam or superabsorbent layer, or a combination thereof.

Referring to FIG. 11B, a PZT pump assembly can be a pump system 6000 incorporated into the dressing assembly 950B. An internal conduit 954B can fluidly interconnect the pump system 6000 with the wound site (e.g., via one or more layers of the dressing 950B). The pump system 6000 can include one or more pump assemblies P (such as the pump assemblies disclosed above). In some embodiments, the pump system 6000 includes an array (such as one of the arrays disclosed above). The dressing 950B can include one or more layer of woven, non-woven foam or superabsorbent layer, or a combination thereof.

Other Embodiments

Embodiments of the pump systems (e.g., pump assemblies, arrays) of the present disclosure are not limited to use with a dressing or for wound therapy. Any of the embodiments of the pump systems disclosed herein can be used independently of a wound dressing. Further, any of the embodiments of the pump systems disclosed herein can be used, or can be adapted for use, for other purposes outside of negative pressure wound therapy. As such, any of the embodiments of pump systems disclosed herein can be used, or can be adapted for use, to move fluids (gaseous and/or liquid) in any system or application.

Any value of a threshold, limit, duration, etc. provided herein is not intended to be absolute and, thereby, can be approximate. In addition, any threshold, limit, duration, etc. provided herein can be fixed or varied either automatically or by a user. Furthermore, as is used herein relative terminology such as exceeds, greater than, less than, etc. in relation to a reference value is intended to also encompass being equal to the reference value. For example, exceeding a reference value that is positive can encompass being equal to or greater than the reference value. In addition, as is used herein relative terminology such as exceeds, greater than, less than, etc. in relation to a reference value is intended to also encompass an inverse of the disclosed relationship, such as below, less than, greater than, etc. in relations to the reference value.

While certain embodiments have been described, these embodiments have been presented by way of example only, and are not intended to limit the scope of the disclosure. Indeed, the novel methods and systems described herein may be embodied in a variety of other forms. Furthermore, various omissions, substitutions and changes in the systems and methods described herein may be made without departing from the spirit of the disclosure. The accompanying claims and their equivalents are intended to cover such forms or modifications as would fall within the scope and spirit of the disclosure. Accordingly, the scope of the present disclosure is defined only by reference to the claims presented herein or as presented in the future.

Features, materials, characteristics, or groups described in conjunction with a particular aspect, embodiment, or example are to be understood to be applicable to any other aspect, embodiment or example described in this section or elsewhere in this specification unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

Furthermore, certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as a subcombination or variation of a subcombination.

Moreover, while operations may be depicted in the drawings or described in the specification in a particular order, such operations need not be performed in the particular order shown or in sequential order, or that all operations be performed, to achieve desirable results. Other operations that are not depicted or described can be incorporated in the example methods and processes. For example, one or more additional operations can be performed before, after, simultaneously, or between any of the described operations. Further, the operations may be rearranged or reordered in other implementations. Those skilled in the art will appreciate that in some embodiments, the actual steps taken in the processes illustrated and/or disclosed may differ from those shown in the figures. Depending on the embodiment, certain of the steps described above may be removed, others may be added. Various components illustrated in the figures may be implemented as software and/or firmware on a processor, controller, ASIC, FPGA, and/or dedicated hardware. Hardware components, such as processors, ASICs, FPGAs, and the like, can include logic circuitry. Furthermore, the features and attributes of the specific embodiments disclosed above may be combined in different ways to form additional embodiments, all of which fall within the scope of the present disclosure. Also, the separation of various system components in the implementations described above should not be understood as requiring such separation in all implementations, and it should be understood that the described components and systems can generally be integrated together in a single product or packaged into multiple products.

For purposes of this disclosure, certain aspects, advantages, and novel features are described herein. Not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, or 0.1 degree.

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

What is claimed is:

1. An apparatus for use in negative pressure wound therapy, comprising:
   a pump system comprising:
      a pump assembly comprising:
         a pump chamber having an interior surface, an exterior surface, a first side, a second side generally opposite the first side, an inlet and an outlet, each of the first side and the second side being moveable;
         a first magnetic actuator coupled to the first side of the pump chamber; and
         a second magnetic actuator coupled to the second side of the pump chamber,
      wherein:
         one or both of the first and second magnetic actuators is an electromagnet that is actuatable to generate a magnetic field that applies a force on one of both of the first and second magnetic actuators to move the pump chamber between an extended position and a collapsed position to pump a fluid through the pump chamber;
         both the first and second magnetic actuators comprise electromagnets; and
         the electromagnets are coils, an inner diameter of one of the coils being larger than outer diameter of another of the coils, allowing said another of the coils to at least partially extend into an opening of said one of the coils during operation of the pump assembly.

2. The apparatus of claim 1, wherein the electromagnet of the first magnetic actuator and the electromagnet of the second magnetic actuator are oppositely wound along a longitudinal axis of the electromagnets, the electromagnet of the first magnetic actuator configured to be supplied with an electric current in a first phase and the electromagnet of the second magnetic actuator configured to be supplied with an electric current in a second phase different than the first phase to operate the pump assembly.

3. The apparatus of claim 1, further comprising a second pump assembly, the second pump assembly comprising:
   a pump chamber having an interior surface, an exterior surface, a first side, a second side generally opposite the first side, an inlet and an outlet;
   a first magnetic actuator coupled to the first side of the pump chamber; and
   a second magnetic actuator coupled to the second side of the pump chamber,
   wherein one or both of the first and second magnetic actuators is an electromagnet that is actuatable to generate a magnetic field that applies a force on one of both of the first and second magnetic actuators to move the pump chamber between an extended position and a collapsed position to pump a fluid through the pump chamber.

4. The apparatus of claim 3, wherein the pump assembly is operated in a first phase and the second pump assembly is operated in a second phase opposite to the first phase to facilitate movement of fluid through the pump system.

5. The apparatus of claim 4, wherein the pump assembly and second pump assembly are operated in a same phase.

6. The apparatus of claim 4, wherein the pump assembly and second pump assembly are arranged in separate layers one on top of the other, the pump assembly being operated in a first phase and the second pump assembly being operated in a second phase opposite to the first phase to facilitate movement of fluid through the pump system.

7. A wound dressing for use in negative pressure wound therapy, comprising:
   a dressing body comprising one or more layers and configured to be removably disposed over a wound; and
   one or more pump assemblies disposed over and fluidically coupled to at least one of said one or more layers and configured to pump a fluid from said wound, each of the one or more pump assemblies comprising:
      a pump chamber defined by an interior surface of a first side and a second side generally opposite the first side, an inlet and an outlet;
      a first magnetic actuator coupled to the interior surface of the first side of the pump chamber; and
      a second magnetic actuator coupled to the interior surface of the second side of the pump chamber,
   wherein each of the first side and the second side is moveable, wherein one or both of the first and second magnetic actuators comprises an electromagnet that is actuatable to generate a magnetic field that applies a force on one of both of the first and second magnetic actuators to move the pump chamber between an extended position and a collapsed position to pump the fluid through the pump chamber.

8. The wound dressing of claim 7, wherein the pump chamber is defined by a first membrane and a second membrane, the first and second membranes made of a flexible material and configured to move toward each other when the pump chamber moves toward the collapsed position and to move away from each other when the pump chamber moves toward the extended position.

9. The wound dressing of claim 7, wherein the one or more pump assemblies comprises one or more one-way valves positioned along a flow path between the inlet and the outlet of the pump chamber.

10. The wound dressing of claim 9, wherein at least one of the one or more one-way valves comprises a material that swells upon contact with a liquid, thereby allowing operation of the one or more pump assemblies to cease upon the dressing body becoming filled with wound exudate.

11. The wound dressing of claim 7, wherein the first magnetic actuator comprises the electromagnet and the second magnetic actuator comprises a permanent magnet.

12. The wound dressing of any of claim 11, wherein the permanent magnet has an annular shape with an inner diameter and an outer diameter, and wherein the electromagnet comprises a coil with an inner diameter and an outer diameter.

13. The wound dressing of claim 12, wherein the inner diameter of the permanent magnet is larger than an outer diameter of the coil, allowing the coil to at least partially extend into an opening of the permanent magnet during operation of the one or more pump assemblies.

14. The wound dressing of claim 12, wherein the outer diameter of the permanent magnet is smaller than an inner diameter of the coil, allowing the coil to at least partially extend over the permanent magnet during operation of the one or more pump assemblies.

15. The wound dressing of claim 11, wherein the permanent magnet comprises a plate.

16. The wound dressing of claim 7, wherein the first magnetic actuator comprises a first electromagnet and the second magnetic actuator comprises a second electromagnet.

17. The wound dressing of claim 16, wherein the first and second electromagnets comprise coils, an inner diameter of one of the coils being larger than outer diameter of another of the coils, allowing said another of the coils to at least partially extend into an opening of said one of the coils during operation of the one or more pump assemblies.

18. The wound dressing of claim 16, wherein the first and second electromagnets are oppositely wound along a longitudinal axis of the first and second electromagnets, the first electromagnet configured to be supplied with an electric current in a first phase and the second electromagnet configured to be supplied with an electric current in a second phase different than the first phase to operate the one or more pump assemblies.

19. The wound dressing of claim 7, wherein the one or more pump assemblies comprise a first pump assembly and a second pump assembly.

20. The wound dressing of claim 19, wherein the first pump assembly is operated in a first phase and the second pump assembly is operated in a second phase opposite to the first phase to facilitate movement of the fluid.

\* \* \* \* \*

UNITED STATES PATENT AND TRADEMARK OFFICE
CERTIFICATE OF CORRECTION

PATENT NO. : 10,973,693 B2  
APPLICATION NO. : 15/574790  
DATED : April 13, 2021  
INVENTOR(S) : Allan Kenneth Frazer Grugeon Hunt Page 1 of 1

It is certified that error appears in the above-identified patent and that said Letters Patent is hereby corrected as shown below:

In the Specification

In Column 12, Line 22, delete "adhesive)" and insert --adhesive--.

In Column 18, Line 49, delete "1810a,b" and insert --1810a, b--.

In Column 20, Line 33, delete "adhesive)" and insert --adhesive--.

In the Claims

In Column 24, Line 47, delete "The wound dressing of any of claim" and insert --The wound dressing of claim--.

Signed and Sealed this  
Twenty-fifth Day of May, 2021

Drew Hirshfeld  
*Performing the Functions and Duties of the*  
*Under Secretary of Commerce for Intellectual Property and*  
*Director of the United States Patent and Trademark Office*